United States Patent
Klippenstein

(10) Patent No.: US 9,192,732 B2
(45) Date of Patent: *Nov. 24, 2015

(54) SINGLE USE PNEUMATIC SAFETY SYRINGE PROVIDING GAS-DRIVEN NEEDLE RETRACTION

(71) Applicant: L.O.M. Laboratories Inc., Calgary (CA)

(72) Inventor: John Klippenstein, West Kelowna (CA)

(73) Assignee: L.O.M. LABORATORIES INC., Vancouver (CA)

( * ) Notice: Subject to any disclaimer, the term of this patent is extended or adjusted under 35 U.S.C. 154(b) by 154 days.

This patent is subject to a terminal disclaimer.

(21) Appl. No.: 13/975,190

(22) Filed: Aug. 23, 2013

(65) Prior Publication Data

US 2013/0345632 A1 Dec. 26, 2013

Related U.S. Application Data

(63) Continuation of application No. 13/430,382, filed on Mar. 26, 2012, now Pat. No. 8,523,810, which is a continuation of application No. 12/780,104, filed on May 14, 2010, now Pat. No. 8,167,848, which is a continuation of application No. 11/219,201, filed on Sep. 2, 2005, now Pat. No. 7,811,259.

(60) Provisional application No. 60/606,891, filed on Sep. 3, 2004.

(51) Int. Cl.
*A61M 5/00* (2006.01)
*A61M 5/32* (2006.01)
*A61M 5/50* (2006.01)

(52) U.S. Cl.
CPC ............. *A61M 5/3234* (2013.01); *A61M 5/502* (2013.01); *A61M 5/508* (2013.01); *A61M 2005/3241* (2013.01)

(58) Field of Classification Search
CPC .................. A61M 5/3234; A61M 2005/3226; A61M 2005/3241; A61M 2005/3242; A61M 5/508
USPC .......... 604/181, 187, 192–198, 110, 218–231
See application file for complete search history.

(56) References Cited

U.S. PATENT DOCUMENTS

| | | |
|---|---|---|
| 5,118,614 A | 6/1992 | Rybak |
| 5,120,310 A | 6/1992 | Shaw |

(Continued)

FOREIGN PATENT DOCUMENTS

| | | |
|---|---|---|
| CN | 2853080 Y | 1/2007 |
| CN | 101193675 A | 4/2008 |

(Continued)

OTHER PUBLICATIONS

Communication pursuant to Article 94(3) EPC for corresponding European Application No. 05778713.7 mailed Feb. 8, 2010, Extended European Search Report and European Seach Opinion mailed Nov. 4, 2009 and the Response thereto filed Jun. 8, 2010.

(Continued)

*Primary Examiner* — Phillip Gray
(74) *Attorney, Agent, or Firm* — Oyen Wiggs Green & Mutala LLP

(57) ABSTRACT

A pneumatic retractable syringe has a plunger having an interior retraction lumen. The plunger and syringe barrel have cooperating locking elements so that the plunger is locked after use within the syringe barrel. After injection of medicament is completed, the needle is retracted into the lumen by compressed gas that is released from a gas cell within the syringe when the gas cell is ruptured just before the plunger reaches the end of its downstream path of travel.

20 Claims, 13 Drawing Sheets

(56) References Cited

U.S. PATENT DOCUMENTS

| | | | |
|---|---|---|---|
| 5,122,118 A | 6/1992 | Haber | |
| 5,176,640 A * | 1/1993 | Nacci et al. | 604/110 |
| 5,188,614 A | 2/1993 | Hart | |
| 5,211,628 A | 5/1993 | Marshall | |
| 5,224,936 A | 7/1993 | Gallagher | |
| 5,334,155 A | 8/1994 | Sobel | |
| 5,389,076 A | 2/1995 | Shaw | |
| 5,407,436 A | 4/1995 | Toft | |
| 5,423,758 A | 6/1995 | Shaw | |
| 5,433,712 A | 7/1995 | Stiles | |
| 5,533,970 A | 7/1996 | Berger | |
| 5,575,777 A | 11/1996 | Cover | |
| 5,578,011 A | 11/1996 | Shaw | |
| 5,632,733 A | 5/1997 | Shaw | |
| 5,702,367 A | 12/1997 | Cover | |
| 5,797,880 A | 8/1998 | Erskine | |
| 5,868,713 A * | 2/1999 | Klippenstein | 604/195 |
| 5,989,220 A | 11/1999 | Shaw | |
| 6,015,438 A | 1/2000 | Shaw | |
| 6,083,199 A | 7/2000 | Thorley | |
| 6,086,568 A | 7/2000 | Caizza | |
| 6,090,077 A | 7/2000 | Shaw | |
| 6,099,500 A | 8/2000 | Dysarz | |
| 6,179,812 B1 | 1/2001 | Botich | |
| 6,183,440 B1 | 2/2001 | Bell | |
| 6,193,695 B1 | 2/2001 | Rippstein | |
| 6,206,853 B1 | 3/2001 | Bonnet | |
| 6,210,371 B1 | 4/2001 | Shaw | |
| 6,221,055 B1 | 4/2001 | Shaw | |
| 6,241,707 B1 | 6/2001 | Dysarz | |
| 6,267,749 B1 | 7/2001 | Miklos | |
| 6,361,525 B2 | 3/2002 | Capes | |
| 6,406,461 B1 | 6/2002 | Ellingsen | |
| 6,409,701 B1 | 6/2002 | Cohn | |
| 6,413,236 B1 | 7/2002 | Van Dyke | |
| 6,413,237 B1 | 7/2002 | Caizza | |
| 6,432,087 B1 | 8/2002 | Hoeck | |
| 6,458,105 B1 | 10/2002 | Rippstein | |
| 6,474,472 B1 | 11/2002 | Shaw | |
| 6,494,863 B1 | 12/2002 | Shaw | |
| 6,558,357 B1 | 5/2003 | Hoeck | |
| 6,572,565 B2 | 6/2003 | Daley | |
| 6,572,584 B1 | 6/2003 | Shaw | |
| 6,585,690 B1 | 7/2003 | Hoeck | |
| 6,599,268 B1 | 7/2003 | Townsend | |
| 6,679,863 B2 | 1/2004 | Bush | |
| 6,692,470 B2 | 2/2004 | Sanpietro | |
| 6,740,062 B2 | 5/2004 | Hjertman | |
| 6,767,335 B1 | 7/2004 | Helg | |
| 6,846,301 B2 | 1/2005 | Smith | |
| 6,868,713 B2 | 3/2005 | Bolz | |
| 6,872,193 B2 | 3/2005 | Shaw | |
| 7,090,656 B1 | 8/2006 | Botich | |
| 7,182,734 B2 | 2/2007 | Saulenas | |
| 7,258,678 B2 | 8/2007 | Wilkinson | |
| 7,294,118 B2 | 11/2007 | Saulenas | |
| 7,344,517 B2 | 3/2008 | Schiller | |
| 7,351,224 B1 | 4/2008 | Shaw | |
| 7,811,259 B2 | 10/2010 | Klippenstein | |
| 8,167,848 B2 | 5/2012 | Klippenstein | |
| 8,523,810 B2 | 9/2013 | Klippenstein | |
| 2003/0040717 A1 | 2/2003 | Saulenas | |
| 2003/0078540 A1 | 4/2003 | Saulenas | |
| 2003/0176843 A1 | 9/2003 | Wilkinson | |
| 2004/0153034 A1 | 8/2004 | Fan | |
| 2005/0159705 A1 | 7/2005 | Crawford | |
| 2005/0159707 A1 | 7/2005 | Schiller | |
| 2005/0215951 A1 | 9/2005 | Saulenas | |
| 2006/0111671 A1 | 5/2006 | Klippenstein | |
| 2008/0208122 A1 | 8/2008 | Walton | |
| 2010/0222739 A1 | 9/2010 | Klippenstein | |
| 2012/0004621 A1 | 1/2012 | Shaw | |
| 2012/0184903 A1 | 7/2012 | Klippenstein | |

FOREIGN PATENT DOCUMENTS

| | | |
|---|---|---|
| EP | 479217 A1 | 9/1991 |
| EP | 596211 A1 | 5/1994 |
| FR | 2831448 A1 | 5/2003 |
| JP | 6142204 A | 5/1994 |
| NL | 9000292 A | 2/1990 |
| WO | 91/04760 A1 | 4/1991 |
| WO | 95/01811 A1 | 1/1995 |
| WO | 98/34659 A1 | 8/1998 |
| WO | 99/25401 A1 | 5/1999 |
| WO | 00/02607 A1 | 1/2000 |
| WO | 01/80930 A1 | 11/2001 |
| WO | 03/051435 A1 | 6/2003 |
| WO | 2004/082747 A1 | 9/2004 |
| WO | 2005/011792 A1 | 2/2005 |
| WO | 2005/070292 A1 | 8/2005 |
| WO | 2005/072801 A1 | 8/2005 |
| WO | 2006/017889 A1 | 2/2006 |
| WO | 2006/024172 A1 | 3/2006 |
| WO | 2006/108243 A2 | 10/2006 |
| WO | 2006/119570 A1 | 11/2006 |

OTHER PUBLICATIONS

Maxxon Applauds New Federal Needlestick Act Press Release, Nov. 2, 2000, Business Wire.

Maxxon Safety Syringe Press Release, Feb. 2000, online: <http://www.micro-stocks.com/Research/MXON.htm>.

Maxxon Announces Safety Syringe Patent Filing, Advance for Respiratory Care Practitioner, Daily News Watch, Feb. 2000, online:<http://www.advanceforrcp.com/previousdnw/rcdnwjan31.html>.

International Search Report and Written Opinion mailed Dec. 2, 2005 for PCT/CA2005/001341 filed Sep. 2, 2005.

Office Action mailed Jan. 11, 2011 for corresponding Japan patent application No. 2007-528545 and English translation thereof, 4 pages.

Office Action mailed Mar. 9, 2009 for U.S. Appl. No. 11/219,201, Klippenstein, filed Sep. 2, 2005 (now U.S. Pat. No. 7,811,259), parent of U.S. Appl. No. 12/780,104 (now U.S. Pat. No. 8,167,848), parent of U.S. Appl. No. 13/430,382 (now U.S. Pat. No. 8,523,810), 6 pages.

Notice of Allowance mailed Jul. 29, 2010 for U.S. Appl. No. 11/219,201, Klippenstein, filed Sep. 2, 2005 (now U.S. Pat. No. 7,811,259), parent of U.S. Appl. No. 12/780,104 (now U.S. Pat. No. 8,167,848), parent of U.S. Appl. No. 13/430,382 (now U.S. Pat. No. 8,523,810).

Supplemental Notice of Allowability mailed Sep. 15, 2010 for U.S. Appl. No. 11/219,201, Klippenstein, filed Sep. 2, 2005 (now U.S. Pat. No. 7,811,259), parent of U.S. Appl. No. 12/780,104 (now U.S. Pat. No. 8,167,848), parent of U.S. Appl. No. 13/430,382 (now U.S. Pat. No. 8,523,810), 5 pages.

Office Action mailed Feb. 4, 2010 and the response thereto filed Apr. 30, 2010 for U.S. Appl. No. 11/219,201, Klippenstein, filed Sep. 2, 2005 (now U.S. Pat. No. 7,811,259), parent of U.S. Appl. No. 12/780,104 (now U.S. Pat. No. 8,167,848), parent of U.S. Appl. No. 13/430,382 (now U.S. Pat. No. 8,523,810).

Office Action mailed Jan. 19, 2011 for U.S. Appl. No. 12/780,104, Klippenstein, filed May 14, 2010 (now U.S. Pat. No. 8,167,848), continuation of U.S. Appl. No. 11/219,201 (now U.S. Pat. No. 7,811,259), parent of U.S. Appl. No. 13/430,382 (now U.S. Pat. No. 8,523,810).

Office Action mailed Jun. 23, 2011 for U.S. Appl. No. 12/780,104, Klippenstein, filed May 14, 2010 (now U.S. Pat. No. 8,167,848), continuation of U.S. Appl. No. 11/219,201 (now U.S. Pat. No. 7,811,259), parent of U.S. Appl. No. 13/430,382 (now U.S. Pat. No. 8,523,810).

Notice of Allowance mailed Mar. 8, 2012 for U.S. Appl. No. 12/780,104, Klippenstein, filed May 14, 2010 (now U.S. Pat. No. 8,167,848), continuation of U.S. Appl. No. 11/219,201 (now U.S. Pat. No. 7,811,259), parent of U.S. Appl. No. 13/430,382 (now U.S. Pat. No. 8,523,810).

(56) References Cited

OTHER PUBLICATIONS

Office Action mailed Jun. 8, 2012 for U.S. Appl. No. 13/430,382, Klippenstein (now U.S. Pat. No. 8,523,810), Klippenstein, filed Mar. 26, 2012, continuation of U.S. Appl. No. 12/780,104 (now U.S. Pat. No. 8,167,848), continuation of U.S. Appl. No. 11/219,201 (now U.S. Pat. No. 7,811,259).

Office Action mailed Dec. 13, 2012 for U.S. Appl. No. 13/430,382 (now U.S. Pat. No. 8,523,810), Klippenstein, filed Mar. 26, 2012, continuation of U.S. Appl. No. 12/780,104 (now U.S. Pat. No. 8,167,848), continuation of U.S. Appl. No. 11/219,201 (now U.S. Pat. No. 7,811,259).

Notice of Allowance mailed May 10, 2013 for U.S. Appl. No. 13/430,382 (now U.S. Pat. No. 8,523,810), Klippenstein, filed Mar. 26, 2012, continuation of U.S. Appl. No. 12/780,104 (now U.S. Pat. No. 8,167,848), continuation of U.S. Appl. No. 11/219,201 (now U.S. Pat. No. 7,811,259).

\* cited by examiner

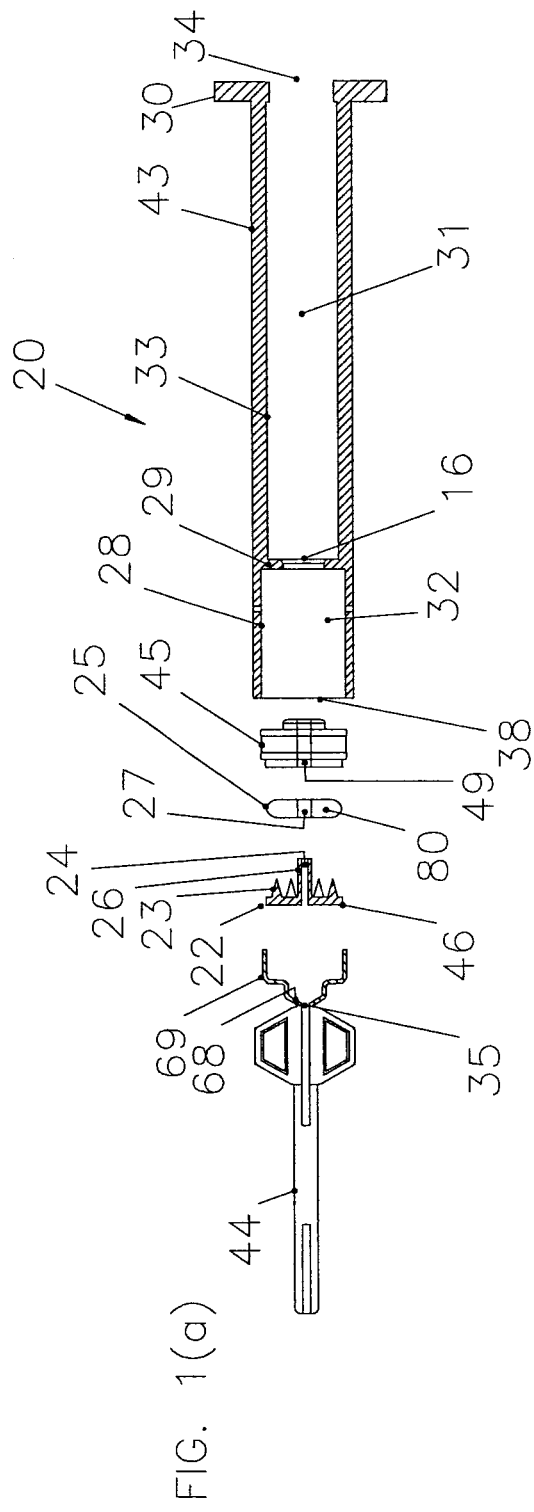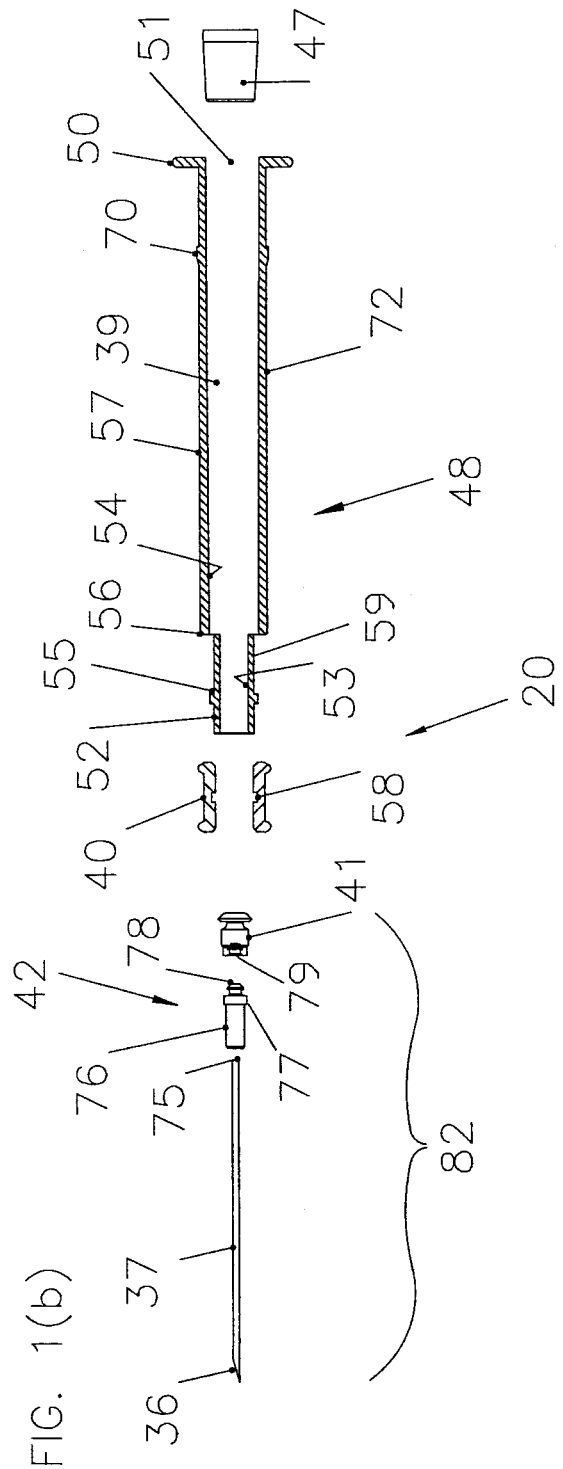
FIG. 1(a)
FIG. 1(b)

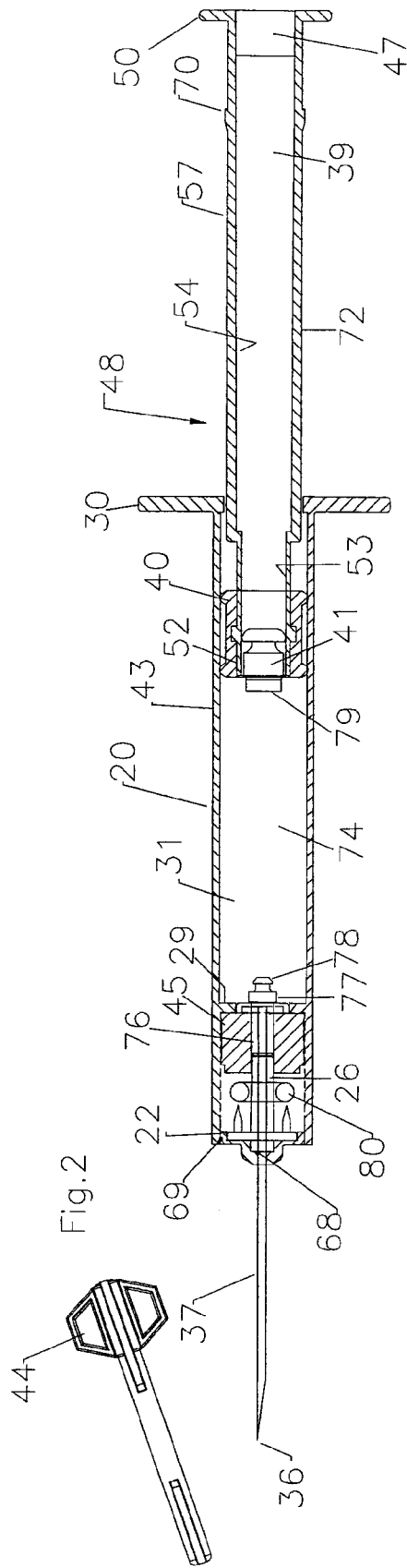

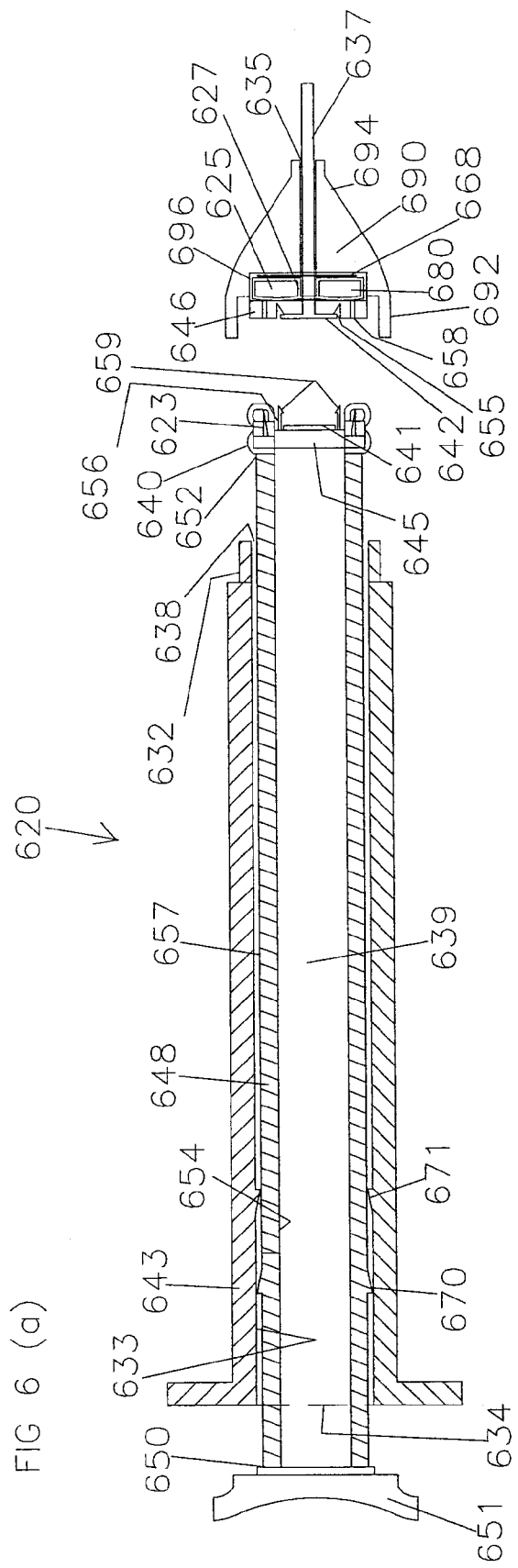

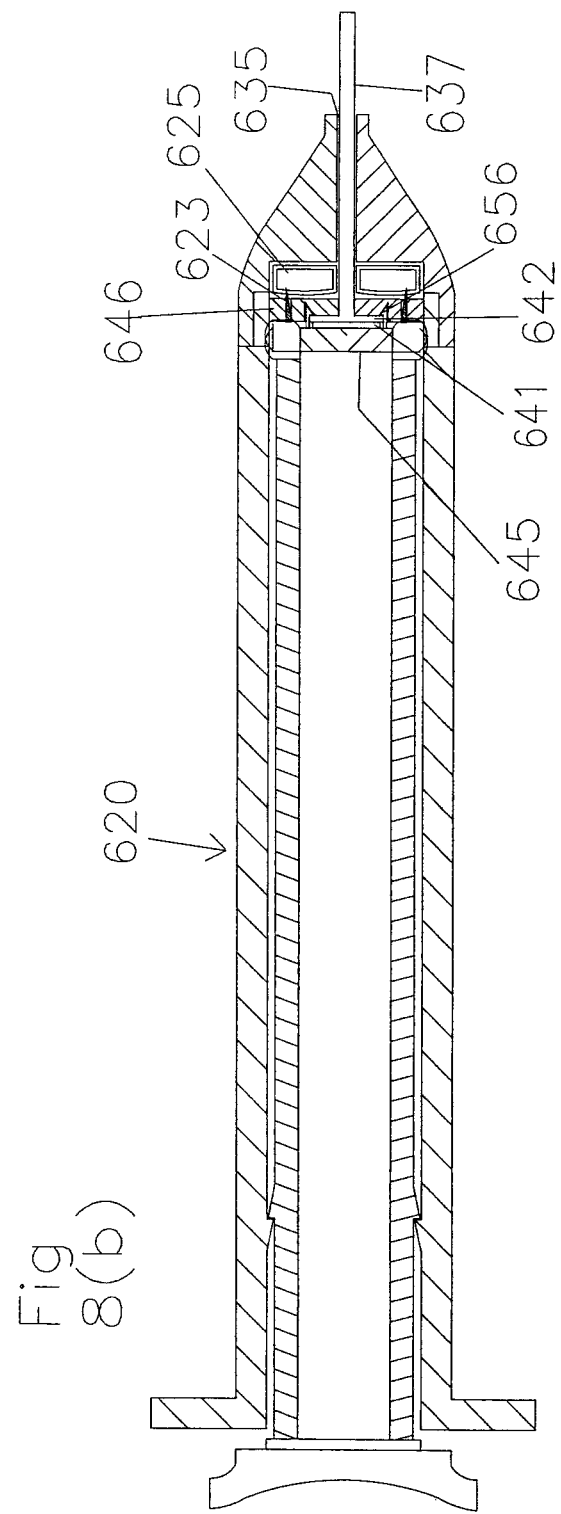

SINGLE USE PNEUMATIC SAFETY SYRINGE PROVIDING GAS-DRIVEN NEEDLE RETRACTION

RELATED APPLICATIONS

This application is a continuation of U.S. patent application Ser. No. 13/430,382, filed 26 Mar. 2012, which is a continuation of U.S. patent application Ser. No. 12/780,104, filed 14 May 2010, now U.S. Pat. No. 8,167,848, which is a continuation of U.S. patent application Ser. No. 11/219,201, filed 2 Sep. 2005, now U.S. Pat. No. 7,811,259, which claims the benefit of U.S. Provisional Patent Application Ser. No. 60/606,891, filed 3 Sep. 2004, each of which is hereby incorporated by reference herein in its entirety.

FIELD OF THE INVENTION

The invention relates generally to a pneumatic safety syringe of the type for use with a hypodermic needle. In a syringe according to the present invention, following use of the syringe, the plunger is locked into the syringe body (barrel) and the needle is retracted into the retraction lumen of the plunger, thereby preventing accidental stabbing after use and unwanted re-extension of the plunger out of the barrel. The retraction of the needle is effected by the release of gas under pressure or other suitable pneumatic means; e.g. obtained by puncturing a gas cell or by causing a chemical reaction that will release gas. A syringe of this general type is sometimes referred to as a "retractable syringe"; what is meant by this term is that the needle retracts within the body of the syringe.

BACKGROUND OF THE INVENTION

It is well known that many dangerous communicable diseases are spread through contacting the body fluids of an infected person. After use of a syringe, residual body fluids are likely to remain on or within the syringe needle. For this reason, syringes are typically intended for a single use only. In order to be handled safely after use, the needle of a syringe must be covered to prevent it from accidentally stabbing a person who is, for example, collecting the syringe for disposal, thereby releasing residual body fluids into such person. Typically, a protective cap is provided with the syringe, which after use of the syringe, can be used to cover the tip of the needle. However, it sometimes happens that persons attempting to cap a used needle miss the cap and accidentally stab themselves, resulting in potential exposure to communicable diseases. Further, spread of communicable and dangerous diseases is effected by drug-addicted individuals sharing and re-using needles and syringes intended for single use.

There have been several attempts to address this problem by incorporating into syringes, mechanisms for retracting the needle into the syringe following use. U.S. Pat. No. 5,334,155 (Sobel, 2 Aug. 1994) discloses a needle guard comprising an evacuated double walled protective sheath. Before use, the partial vacuum within the protective sheath causes the sheath to fold inwardly upon itself so that the needle extends beyond the protective sheath and may be used for injections. Subsequent to injection, the double wall of the protective sheath can be breached in one place so that the inside of the protective sheath reaches atmospheric pressure. The protective sheath then extends to cover the projecting needle. However, the protective sheath may interfere with use of the syringe as it may obstruct the view of the point the needle is to be inserted into the patient. In addition, it is inconvenient to use; after injection, the user must change the user's hand position on the syringe in order to breach the double wall and activate the sheath. In this manner activation of the safety mechanism is not automatic following injection of the medicament.

The protective safety device shown in U.S. Pat. No. 5,188,614 (Hart, 23 Feb. 1993) is a hollow cylindrical casing that encompasses the syringe. A dual component foaming agent is disposed at the downstream end of the casing. Following injection, the two components of the dual component foaming agent are mixed, creating an expanding foam mixture that forces the syringe back within the casing and encompasses the needle. However, this device suffers from the disadvantages that the casing may interfere with the use of the syringe in making injections as it is designed to fit over a conventional syringe thereby changing the size and feel of the device as compared to a conventional syringe. In addition, a considerable amount of material is necessary in order to make the protective sheath, increasing the expense of both making and disposing of the device.

U.S. Pat. No. 6,193,695 (Rippstein, 27 Feb. 2001) discloses a safety syringe comprising a vacuum chamber on the upstream side of the plunger head. Following injection of medicament, the plunger head engages the needle head, the ambient atmospheric pressure external to the needle head acts on the needle head, forcing the needle and plunger back against the vacuum into the syringe body. The plunger arm may then be snapped off by the user to prohibit further use of the needle. This device suffers from the disadvantage that accidental re-extension of the needle is possible if the plunger arm is not snapped off by the user. A further disadvantage of this device is that if the user does not apply a constant injection force, there is the possibility that the plunger will retract under the vacuum before the medicament is completely injected, thereby causing the syringe to work in reverse.

U.S. Pat. No. 6,413,236 (Van Dyke, 2 Jul. 2002) discloses a safety syringe comprising a vacuum chamber on the upstream side of the plunger head. Following injection of medicament, the plunger head engages the needle head, and the ambient atmospheric pressure external to the needle head acts on the needle head, forcing the needle and plunger back against the vacuum into the syringe body. In this patent, in contrast to U.S. Pat. No. 6,193,695, the needle is lodged in the syringe body at an angle so that the piercing tip end of the needle is pressed against the inner surface of the syringe prohibiting re-extension of the needle even though the plunger arm is fully extended outside the syringe body. However, this device still has the disadvantage that if the user does not apply a constant injection force, there is the possibility that the plunger will retract under the vacuum before the medicament is completely injected, thereby causing the syringe to work in reverse.

The device disclosed in U.S. Pat. No. 5,868,713 (Klippenstein, 9 Feb. 1999) embodies a significant improvement over the previous syringe technology. This earlier Klippenstein syringe includes a gas reservoir that contains a non-toxic compressed gas. Once the gas reservoir is ruptured by the needle header when the needle header is forced in a downstream direction, the released non-toxic compressed gas provides an upstream biasing pressure that biases the needle header and plunger to slide upstream, retracting the needle into the syringe body. A locking mechanism prevents downstream motion of the plunger after retraction of the needle. However, at the end of the retraction phase, the plunger continues to extend outside the barrel of the syringe, thus requiring the user to have changed his hand position by moving his thumb away from the thumb button at the end of the plunger. Further, due to the retention of the plunger in the locked extended position after retraction, the extended syringe takes more space in disposal containers than do conventional syringes. It is an objective of the present invention to overcome these and other disadvantages associated with this prior Klippenstein design.

A syringe designed to provide an optimal solution to the problem of prevention of accidental needle stabbing after the use of the syringe for injection would include the following characteristics:
1. The syringe mechanism should be relatively simple, in that it should be made from as few moving parts as possible consistent with its design objectives, and should be simple to operate, preferably with the look and feel of a conventional syringe.
2. The syringe mechanism should reliably retract the needle or otherwise reliably shield the needle after use, so that accidental stabbing is prevented.
3. The syringe should be relatively inexpensive to manufacture.
4. There should be a minimum of waste plastics and other materials to be disposed of after use of the syringe.
5. Safety-related means should not appreciably interfere with the feel of the syringe in the user's hand.
6. Once the needle has been retracted or shielded, a reliable safety device should prevent the needle from becoming once again exposed.

Note that simplicity of structure and operation, objective 1 above, may contribute to the achievement of the other five objectives listed above.

SUMMARY OF THE INVENTION

A principal objective of the present invention is to provide a syringe of the type for use with a hypodermic needle in which, after injection of medicament is complete, the needle is automatically retracted into the retraction lumen of the plunger and the plunger is locked within the syringe body (barrel). Further objectives include the elimination or reduction of disadvantages associated with prior syringe designs, including the prior Klippenstein syringe disclosed in U.S. Pat. No. 5,868,713.

A safety syringe according to the invention comprises a syringe barrel, plunger, and means for assembling a needle in the syringe. (The needle may be part of the complete assembly or may be installed later, depending upon the design selected.) The gross structural characteristics and operating characteristics of syringes according to the invention may be generally similar to those of prior designs, except as herein described. Among the principal characteristics of syringes of the present invention that differentiate them from prior syringes are the following:

a. The plunger, axially movable within the barrel, has therewithin an axially extending retraction lumen open at its distal end to receive the needle after use of the syringe. The lumen is dimensioned to receive sufficient of the combined length of the needle and the needle carrier to be mentioned below that, after retraction, the needle point remains within the plunger lumen.

b. A gas release cell is located within the assembled syringe distally of the plunger. The gas release cell, which in relation to the preferred embodiments illustrated contains gas under pressure and is sometimes referred to herein as a gas cell, is intact and inoperative prior to substantial completion of injection of medicament by downstream motion of the plunger. For use in the preferred embodiments described in detail below, the gas cell is preferably a discrete self-contained component separately assembled into the syringe and containing suitably selected non-toxic non-corrosive gas under pressure. The gas cell is preferably rupturable to release the gas, but instead may comprise initially separated chemical constituents which may be controllably mingled after substantial completion of injection thereby to cause a chemical reaction that releases gas under pressure.

c. A gas release trigger means located within the assembled syringe between the distal end of the plunger and the gas release cell is operable, in response to downstream motion of the plunger as it approaches its downstream limit of travel, to cause the gas release cell to release gas into the interior of the syringe. In the preferred embodiments described herein for use with a discrete rupturable gas cell, the gas release trigger means preferably comprises a perforator having puncture lances, but instead could comprise tearing or crushing means for breaching the wall of the gas cell. If an alternative gas release cell is employed, such as a two-compartment cell, each compartment containing a separate chemical constituent, the constituents when mingled causing a chemical reaction that releases gas under pressure, then the gas release trigger could comprise, for example, means for rupturing a dividing wall between the two compartments after substantial completion of injection, and then concurrently or preferably shortly thereafter rupturing the outer wall of the gas release cell.

d. A needle carrier is coupled to the needle in the vicinity of the proximal end of the needle. The needle carrier is movable axially within the plunger lumen and has a distal bearing surface against which gas under pressure may bear. The needle carrier moves into the plunger lumen under gas pressure, carrying the needle with it, so as to retract the needle into the lumen. (Of course, there must be a suitable flowpath available for the gas to reach the needle carrier. In some cases, it may be desirable to constrict the flowpath to avoid a sudden surge of pressurized gas against the bearing surface of the needle carrier.) The needle may be formed so as to have a needle header at its proximal end or may be otherwise fixed to a needle header located at or near the proximal end of the needle. The needle carrier in such latter instances may be fixed or coupled to the needle header. The needle carrier preferably includes a sealing element slidingly engaging the walls of the lumen. Because in one preferred embodiment the lumen is constricted at its distal end, the sealing element in such embodiment should be resiliently expandable in diameter to provide a sealing contact with the walls of the large-diameter portion of the lumen once it moves upstream from the constricted distal portion of the lumen.

e. In addition to the needle carrier, whose design enables it to provide an acceptable level of gas sealing upstream of the gas under pressure, one or more further gas barriers are provided for preventing or impeding unwanted escape of gas from the syringe prior to full needle retraction. At least some of the gas barriers may be provided by suitably snug or tight fits between mating components. In some cases, sliding engagement of parts is sufficiently close that serious loss of gas is prevented. Some of these barriers may also serve to block unwanted escape of medicament from the syringe. The objectives are, of course, (i) to have substantially all of the medicament in the syringe injected into the patient and not to leak out of the syringe, and (ii) to have gas pressure drive the needle carrier into the plunger lumen after injection so that the needle becomes fully retracted, and not to have the pressurized gas dissipate before the needle-retraction phase of syringe operation is complete.

f. A needle re-emergence barrier is preferably provided for preventing or impeding downstream movement of the needle following its retraction into the lumen.

Of course, the principal function of the syringe, viz to draw medicament into the barrel and then to inject the medicament into a patient, must not be significantly impeded by incorporation into the syringe of the inventive features of the present invention. To this end, for example, upstream motion of the needle and needle carrier into the lumen must be impeded during filling of the syringe barrel with medicament and injection of medicament into the patient. To a major and possibly a complete extent, depending upon the specific syringe design elected, friction and hand pressure on the plunger may serve to meet the foregoing objectives.

The design of the gas flow path, the components and surfaces responsive to gas pressure, and the gas and liquid blocking elements in any implementation of a syringe design according to the invention should be effective to enable normal medicament charging and normal medicament injection phases of operation without appreciable risk of loss or leakage of medicament and without appreciable interference with normal operational look and feel of the syringe. The foregoing objectives are common to syringe designs of many types and should be readily addressable by any competent syringe designer with the assistance of the present description. Note that the syringe according to the invention should be designed so that the gas pressure is effective during the needle-retraction phase of operation to drive the needle into the plunger lumen, but not to drive the plunger upstream out of the barrel. To this end, the needle must be attached or coupled to a movable element responsive to the gas pressure; both that element and the needle must under gas pressure freely enter and travel upstream into the plunger lumen. When the movable element is forced upstream, the needle perforce travels with it. Further, the syringe must be designed so that the gas released from the gas release cell can reach the movable element and be able to apply an effective upstream force to it. During the retraction of the needle, upstream motion of the plunger should be impeded by the interaction or engagement of the component parts of the syringe and not merely by hand pressure of the user. Escape of gas downstream through the needle aperture and out of the syringe would be wasteful and inefficient, and should be prevented or impeded while the needle is being retracted. Once the needle has been retracted, its re-emergence from the plunger lumen should be blocked.

For realization of some of the principal advantages of preferred embodiments of the invention, a syringe according to the invention also comprises a plunger lock for impeding or preventing unwanted re-extension of the plunger out of the barrel after use of the syringe. The plunger lock comprises a plunger engagement element fixed to the plunger and a cooperating engagement element fixed to the barrel. The engagement elements are located so as to make engaging contact with one another near the downstream limit of travel of the plunger. Further downstream motion of the plunger past the point of engaging contact causes the locking of the plunger within the syringe at or near the downstream limit of travel of the plunger. In order to prevent unwanted gas-driven upstream displacement of the plunger prior to its locking, the plunger lock may be structured to lock the plunger to the barrel at a point in the downstream path of travel of the plunger slightly upstream of the point at which the gas release trigger means operates to cause the gas release cell to release gas. However, because the depression of the plunger to its downstream limit is usually effected in a continuous hand-driven motion, the momentum of that motion is normally sufficient to lock the plunger to the barrel and to rupture the gas release cell, whether the plunger locking precedes the rupturing or is substantially coincident with rupturing or even if the rupturing slightly precedes the plunger locking.

A syringe according to the invention may additionally have a needle re-emergence barrier located downstream of the tip of the needle after the needle has been retracted into the plunger lumen, for preventing or impeding downstream movement of the needle following its retraction into the lumen. This barrier may preferably be a suitable needle port closure means.

In some preferred embodiments of the inventive syringe, the barrel is divided internally into a smaller downstream chamber for housing the gas release cell and gas release trigger means, and an upstream chamber for containing medicament to be injected, the said chambers being separated by a radial chamber separator wall having an axial opening therein for discharge of medicament from the upstream chamber into the needle and for receiving the needle into the plunger lumen after injection.

The inventive syringe in the foregoing embodiments may further comprise within the downstream chamber an engagement ring slideably but with friction engaging the interior circumferential wall of the downstream chamber and axially movable therein. The engagement ring should be relatively immobile within the downstream chamber unless subjected to deliberately applied force. The engagement ring is located between the gas release cell and the radial separator wall and has a central aperture through which medicament from the upstream chamber into the needle may flow and through which passage of the needle into the plunger lumen occurs after injection. The engagement ring provides a buffer against which the gas cell is constrained so as to facilitate rupture of the gas cell by the perforator. The engagement ring engages the needle header to provide support thereto and facilitates alignment of the needle and the needle header within the downstream chamber. Optimally, the distal end of the plunger engages the upstream end of the engagement ring near the downstream limit of travel of the plunger, forcing the gas release cell into rupturing contact with the perforator upon completion of downstream movement of the plunger.

First Exemplary Embodiment

In one embodiment of the present invention, a single-use needle-retracting pneumatic safety syringe, for reducing the risk of accidental needle stabbing after use, comprises a syringe barrel, and operatively located within or partially within the barrel, the following components: a hollow plunger whose hollow interior defines a retraction lumen, a needle port seal, a needle header for holding a needle, a slideable displaceable cylindrical object with a central axial opening (hereinafter frequently and whimsically referred to as an "engagement ring", for reasons to be described below), a gas cell, a perforator, and a plunger lock. The syringe barrel is hollow and has an upstream barrel opening and a downstream barrel opening axially opposed to the upstream barrel opening. The plunger is dimensioned and configured to mate with the interior of the syringe barrel and is mounted for axial movement within the syringe barrel. The plunger has an upstream plunger end having a plug opening to receive a plug, the upstream plunger end projecting from the upstream opening of the syringe barrel, and a downstream plunger end. The downstream plunger end is of a narrower diameter than most of the length of the plunger barrel. The inner diameter of the plunger end is selected so that the needle port seal fits snugly within the downstream plunger end during the injection phase.

During the retraction phase following injection, the needle port seal is forced upstream into the retraction lumen of the plunger by the release of gas under pressure from the gas cell at the end of the plunger downstroke, as will be further described. The needle port seal frictionally engages the inner surface of the downstream end of the plunger, thereby impeding leakage of medicament past the needle port seal into the retraction lumen during administration of the medicament. The retraction lumen within the plunger is bounded by the needle port seal, the upstream plunger end and the inner surface of the plunger. The plug opening provides an opening whereby tools can be inserted to access the internal parts of the syringe during assembly in order to facilitate assembly of the component parts of the syringe. After assembly of the syringe, a plunger plug is snapped into the plug opening, thus sealing the retraction lumen of the plunger. A slideable plunger seal surrounds and is affixed to the downstream plunger end. The dimensions and material of the plunger seal are selected so that the plunger seal slidingly contacts the inner surface of the syringe barrel, (i) impeding leakage of medicament past the plunger seal, while (ii) permitting longitudinal displacement of the plunger.

The displaceable engagement ring slidingly but frictionally engages the inner surface of the syringe barrel and is located downstream of the plunger seal. The engagement ring is dimensioned and configured to mate with the interior of the syringe barrel and is positioned for limited axial displacement within the syringe barrel. To this end, the interior of the syringe barrel is divided axially into a longer upstream chamber and a shorter downstream chamber separated by a chamber separator wall having a central opening large enough to permit the narrow downstream end of the plunger to pass therethrough. Progressing from upstream to downstream within the downstream chamber are located (i) the engagement ring, embracing within its central opening in mating engagement the perforator neck and the needle header body; (ii) the gas cell; and (iii) the perforator body and puncture lances with the points of the latter facing the gas cell.

The engagement ring is not displaced from its initial rest position against the chamber separator wall until the end of the injection phase, whereafter the user's hand pressure applied to the plunger causes the plunger to continue to move axially downstream, resulting in the downstream end of the plunger impinging on the engagement ring and forcing the engagement ring to move axially downstream. This post-injection displacement of the engagement ring forces downstream displacement of the gas cell, thereby forcing the adjacent perforator and gas cell into contact with one another, ultimately causing the rupture of the gas cell by the perforator, whereupon the compressed gas that had been stored in the gas cell is released, forcing retraction of the needle into the retraction lumen, as described in more detail elsewhere in this description.

The hollow needle header is mounted in the central opening of the engagement ring. The diameter of the needle header is chosen such that a compression seal between the needle header and the engagement ring is created by forcing the needle header into the inner opening of the engagement ring during assembly, thereby prohibiting leakage of medicament downstream of the engagement ring between the engagement ring and needle header. A hollow needle is cemented or otherwise affixed to the downstream end of the needle header. When the syringe is charged with medicament, the medicament is confineable within the syringe barrel downstream of the plunger seal and needle port seal and upstream of the engagement ring and needle header. In one embodiment of the invention, the needle header is situated within the engagement ring in such a manner that the upstream portion of the needle header projects upstream out of the central opening of the engagement ring.

The engagement ring serves several purposes, viz
(a) by means of its engagement with the surrounding cylindrical wall of the syringe barrel, it provides stability and provides a compression seal to impede unwanted spurious fluid flow;
(b) by means of the engagement of its central axial opening with the needle header, it holds the needle header and needle in place during injection of medicament into the patient;
(c) by means of the engagement of its central axial opening with the perforator neck and the engagement of that neck with the needle header, it prevents premature puncture of the gas cell by the perforator;
(d) by means of the foregoing engagements, it facilitates radial alignment of the gas cell and the perforator, promoting even positioning of the gas cell relative to the puncture lances, which in turn facilitates optimal puncturing of the gas cell at the end of the plunger downstroke;
(e) it facilitates accurate alignment of the needle port seal with the needle header, in turn facilitating precise connection of the needle port seal to the needle header and thereby facilitating precise retraction of the needle; and
(f) by means of its engagement with and displacement of the gas cell at the end of the plunger downstroke, displacing the gas cell downstream into rupturing contact with the perforator, it effects the release of compressed gas, thereby in turn causing retraction of the needle assembly into the retraction lumen of the plunger.

In this embodiment, the annular gas cell containing compressed gas is mounted within the syringe barrel downstream of the engagement ring. The gas cell is dimensioned and configured to fit within the syringe barrel. A perforator is mounted downstream of the gas cell. The perforator may either be cemented or otherwise affixed to the inner surface of the syringe barrel downstream of the engagement ring or the perforator may be cemented or otherwise affixed to a needle aperture mount which is cemented or otherwise affixed to the downstream barrel opening of the syringe. The perforator comprises one or more puncture lances, a neck, and an inner opening. The puncture lance(s) is/are mounted on the perforator in such a manner that the puncture lances project upstream from the perforator towards the gas cell. The neck of the perforator is mounted in such a manner that the neck projects upstream from the perforator and through the annular opening of the gas cell and into the inner opening of the engagement ring thus making contact with the needle header. The neck of the perforator allows for precise alignment of the needle header, gas cell and puncture lances and prevents downstream motion of the needle header and needle. The orientation of the perforator could if desired be reversed so that the puncture lances project downstream toward a gas cell located downstream thereof.

The perforator mount is provided with a needle aperture and a needle membrane, the latter serving as a needle port closure. The needle is mounted such that it passes through the inner opening of the perforator, through the needle membrane and projects out of and downstream of the needle aperture. The needle membrane is fixed to the needle aperture mount at and around the needle aperture and preferably is tapered about 30° to the axial where the needle membrane contacts the needle. Once the needle has been retracted, the needle membrane covers the needle aperture so as to impede the re-extension of the needle through the needle aperture. The needle aperture mount is cemented or otherwise affixed to a needle cover which provides a protective sheath for the needle prior to use and which may be twisted off, snapped off or otherwise removed from the needle aperture mount prior to use of the syringe so that the needle is exposed for use. The needle cover, perforator mount and perforator may be manufactured as separate pieces or they may be manufactured as one piece; in the latter case, there should be a capability of the needle cover to be twisted or broken off from the perforator mount without causing damage to the perforator prior to use.

In operation, after the syringe is charged with medicament, when a user applies an injection force to the plunger, the plunger seal at the downstream end of the plunger imparts a downstream biasing pressure to the medicament contained in the syringe barrel between the plunger seal and the engagement ring. This downstream biasing pressure applied to the plunger by the user is sufficient to force the medicament through the upstream intake of the needle and into a patient via the downstream tip of the needle. The releasable frictional force securing the engagement ring to the inner surface of the syringe barrel resists the downstream biasing pressure exerted on the engagement ring by the medicament as the medicament is forced through the upstream intake of the needle.

When essentially all of the medicament has been delivered to the patient, further downstream motion of the plunger forces the needle port seal, located at the downstream plunger end, to seal the needle header such that no further medicament or other fluids may be forced through the upstream intake of the needle and delivered to the patient. Further downstream force applied by the user to the plunger (the post-injection force) overcomes the releasable frictional force securing the engagement ring to the inner surface of the syringe, thereby permitting the engagement ring to slide axially downstream within the syringe barrel under hand pressure. Downstream motion of the needle header, however, is constrained by the neck of the perforator contacting the needle header. When the needle header contacts the neck of the perforator projecting upstream of the perforator, further downstream motion of the needle header is prevented. Continued application of a post-injection force on the plunger causes the engagement ring to slide axially downstream and contact the gas cell, thereafter forcing the gas cell to move downstream, eventually resulting in the gas cell impinging on the puncture lance(s) of the perforator. The puncture lances rupture the gas cell, resulting in the release of the non-toxic compressed gas from the gas cell into the syringe barrel in the area confined by the perforator, the engagement ring and the needle port seal.

The released compressed gas is confined within the syringe barrel. Its purpose is to provide an upstream biasing pressure within the syringe barrel upstream of the gas cell with sufficient pressure to overcome the frictional force between the needle port seal and the downstream plunger end. The upstream biasing pressure biases the needle port seal to slide upstream into the retraction lumen of the plunger. During this upstream motion of the needle port seal, the needle port seal remains coupled to the needle header, which is cemented or otherwise fixed to the needle, thereby affecting retraction of the needle into the retraction lumen. The released gas remains under pressure and generates a corresponding upstream biasing pressure that acts on the needle port seal, biasing the needle port seal, needle header and needle to slide upstream within the retraction lumen of the plunger, thereby effecting retraction of the needle within the retraction lumen.

Corresponding upstream motion of the plunger is prevented or impeded by a plunger lock that engages when the plunger has reached its downstream limit, thereby locking the plunger within the syringe barrel. In a preferred embodiment, a circumferential plunger verge is located on the outer surface of the plunger and is configured to have a shallow downstream side and a steep upstream side such that when a downstream force is applied to the plunger, the shallow downstream side of the plunger lock slides downstream of the upstream barrel opening of the syringe barrel, which is of a slightly smaller diameter than the outer diameter of the plunger. When the gas cell is ruptured releasing the compressed gas, the upstream biasing pressure resulting from release of the compressed gas is insufficient to force the steep upstream side of the plunger verge to move upstream past the upstream barrel opening of the syringe barrel. The shallow downstream side of the verge permits the plunger to slip downstream relatively easily past the upstream barrel opening.

There has to be enough gas under pressure in the gas cell such that the upstream biasing pressure is sufficient to generate enough force to move the needle port seal to move upstream through the required distance. In syringes designed for evaluation as pre-manufacture prototypes, typical values for the gas pressure in the gas cell are expected to range from about 5 to about 20 p.s.i.g; the pressure preferably would not exceed about 9 p.s.i.g. Note that the speed and reliability of needle retraction are heavily dependent upon the gas pressure selected; an empirical approach should be taken. The gas pressure should be sufficient to retract the needle relatively quickly but should not be excessive to the point that the gas discharge upon puncture is unduly shocking to the user or to the component parts of the syringe, nor should the needle retraction cause splattering of bodily fluids. These objectives are readily achievable in syringes constructed in accordance with the present invention, particularly in contrast to previous designs in which the needle retraction was effected by spring action.

Preferably, most of the component parts of the syringe are fabricated from plastics materials. Preferably the needle port seal, engagement ring and the plunger seal are fabricated from rubber or the like as these components function better if made from a more flexible material than the syringe barrel. All rubber parts within the syringe are coated with a medical fluid lubricant as typically used in the industry. Typically, the needle will be made of stainless steel or a specialty hard, strong plastics material.

The foregoing syringe embodiment of the present invention can be adapted for multiple volume sizes of syringes including, but not limited to, 1, 1.5, 2, 3, 5, 10 and 20 mL syringes.

Second Exemplary Embodiment

In a second embodiment of the present invention, the syringe manifests a few significant modifications relative to the first exemplary embodiment of the invention described above. In particular, the engagement ring is modified and elongated such that the needle header, including the upstream end of the needle header, may be positioned within the central cylindrical opening of the engagement ring in such a manner that the upstream end of the needle header is flush with the upstream end of the engagement ring. Further, the needle port seal is initially mounted in the downstream end of the plunger such that the downstream end of the needle port seal is flush with the downstream limit of the downstream end of the plunger. These modifications allow for better alignment of the needle port seal with the needle header during the post-injection phase of the operation of the syringe relative to the first embodiment, thus resulting in a more accurate coupling mechanism between the needle port seal and the needle header as compared with the first embodiment.

In this second embodiment, the plunger lock functions in a manner generally similar to the functioning of the plunger lock of the first embodiment, but instead of using the upstream barrel opening of the syringe barrel as an element of the lock, there is provided on the interior surface of the barrel a circumferential verge similar in design to the verge on the outer cylindrical surface of the plunger, but sloped in the opposite sense. The two verges are positioned to engage one another just before the plunger reaches its downstream limit of travel. The shoulder-to-shoulder engagement of the two verges in that locking position is secure against all but high disruptive forces applied to the syringe.

Third Exemplary Embodiment

In a third syringe embodiment of the present invention, the perforator, rather than being located downstream of the gas cell and having puncture lances that project upstream from the perforator towards the gas cell, is mounted on the downstream plunger end and has puncture lances that project downstream from the downstream plunger end towards the gas cell.

An engagement disc is positioned within the downstream end of the plunger and prevents medicament from entering the retraction lumen of the plunger during injection of the medicament into a patient. A needle port seal is fixed to the downstream end of the engagement disc. Further, a header lock is fixed to the engagement disc and projects downstream from the engagement ring. In the embodiment illustrated, the header lock comprises projecting barbed lances whose barbs grip the needle header. When the engagement disc retracts into the plunger, it carries with it the disc-shaped needle header and consequently the needle.

A hollow needle end cap is dimensioned and configured to mate with the downstream end of the syringe barrel. The needle end cap has a needle aperture oriented to be axially aligned with and opposed to the upstream barrel opening of the syringe barrel.

An alignment disc is securely mounted in the needle end cap near the upstream end of the needle end cap such that a gas cell chamber for containing the gas cell is formed between the base of the needle end cap and the downstream end of the needle end cap. The alignment disc has a central needle aperture and a circular recessed groove concentric with the central aperture of the alignment disc. The recessed groove is dimensioned and configured to receive the header lock lances when they move downstream to grip the needle header. The needle end cap is provided with one or more through holes dimensioned and configured to allow the puncture lances affixed to the downstream plunger end to pass therethrough.

Preferably, a needle membrane is fixed to the needle end cap at and around the needle aperture. The needle membrane serves as a needle port closure.

Advantages of the Invention

It is an advantage of this invention that, once the needle has been retracted into the plunger lumen, the needle and any parts attached to it are completely detached from the distal end of the syringe barrel and from the distal end of the syringe plunger, and are retained in place within the plunger lumen.

It is an advantage of this invention that the safety mechanism is relatively simple to operate in that drawing medicament into the syringe and injecting medicament into the patient are substantially conventional. To initiate the needle-retraction phase of syringe operation, the user need only continue to apply a downstream force to the plunger to move the plunger through a further short displacement after the medicament has been substantially discharged from the syringe. The gross structure of the syringe incorporating the needle-retraction elements need not appreciably change the look and feel of syringes according to the invention as compared to the look and feel of a conventional syringe; this feature is common to the earlier Klippenstein syringe discussed briefly above, and contrasts with the safety mechanisms incorporated into the designs disclosed in U.S. Pat. Nos. 5,334,155 and 5,188,614.

It is a further advantage of preferred embodiments of this invention that in the needle-retraction phase of syringe operation, the needle is reliably retracted into the syringe barrel, and the plunger is reliably prevented from re-extending out of the barrel. Severe force would be required to defeat or reverse these two results. The needle retraction time, that is, the time required to retract the needle into the syringe, may be reliably controlled by selecting the pressure of the gas loaded into the gas cell during manufacture of the gas cell.

It is a further advantage of preferred embodiments of this invention that the safety mechanism, i.e. the operative needle-retraction and plunger lock components, employs a small number of moving parts. The simplicity of the design and the small number of moving parts of preferred embodiments of the syringe of the invention allows the use of the syringe in a broad range of climatic and temperature conditions. Further, material costs are reduced in the design of preferred embodiments of the inventive syringe due to the simplicity of the design and further due to the absence of mechanical parts found in other safety syringes, such as springs and metal sheaths. The need for such components in other safety syringes often requires considerable play between the syringe plunger and the syringe barrel of such other syringes, interfering with optimum fit of plunger with barrel for injection purposes.

It is a further advantage of preferred embodiments of this invention that the safety syringe according to the invention may be mass-produced on an automated assembly line (not per se constituting an aspect of this invention), thereby minimizing some labor costs associated with other needle-retraction syringes at present available in the industry. In particular, it is a feature of this invention that the gas cell of the invention may be manufactured separately from other component parts of the safety syringe according to the invention, and can therefore be loaded into the syringe on an automated assembly line, thereby facilitating a reduction in the use of relatively costly manual labor. This means that the syringe is relatively inexpensive to manufacture.

After the needle-retraction phase is complete, the component parts of the syringe of the invention are situated in a relatively compact terminal formation as compared to the component parts of the syringes described in U.S. Pat. Nos. 5,868,713 and 6,413,236, thus allowing for ease of disposal of syringes according to the invention. The compact assembly of the component parts of the syringe following the retraction phase is achieved automatically once the needle-retraction phase has commenced, and without the need for further intervention by the user as is required in the use of syringes described in U.S. Pat. No. 6,193,695.

The syringe of the present invention is designed such that the needle-retraction phase cannot commence until the injection phase is substantially complete, in contrast to the designs of the syringes disclosed in U.S. Pat. Nos. 6,193,695 and 6,413,236. In accordance with the present invention, the needle-retraction phase is initiated automatically upon completion of the injection phase and does not require the user to change his or her hand position, as is required to initiate the safety phase of syringe operation disclosed in U.S. Pat. Nos. 5,334,155; 6,193,695; 6,413,236; and 5,868,713.

Other advantages of syringes according to the invention will be apparent from a reading of detailed descriptions of preferred embodiments, below.

BRIEF DESCRIPTION OF THE DRAWINGS

The present invention may be further understood from the following detailed description with reference to the accompanying drawings in which all views are schematic.

FIG. 1(a), in exploded longitudinal section view, illustrates the barrel, gas cell, perforator therefore, needle cover, and engagement ring of a single-use pneumatic retractable syringe in accordance with a preferred embodiment of a syringe made In accordance with the invention.

FIG. 1(b), in exploded longitudinal section view, illustrates the plunger, plunger seal, needle and needle header for use with the syringe components illustrated in FIG. 1(a).

FIG. 2, in longitudinal section view, illustrates the syringe of FIGS. 1(a) and 1(b) fully assembled, with the plunger extended upstream out of the syringe barrel so that medicament can be drawn into the syringe.

FIG. 8(b), in longitudinal section view, illustrates the syringe of FIG. 6(a) with the plunger fully depressed and locked within the barrel of the syringe.

DETAILED DESCRIPTION OF THE INVENTION

Figure 3:
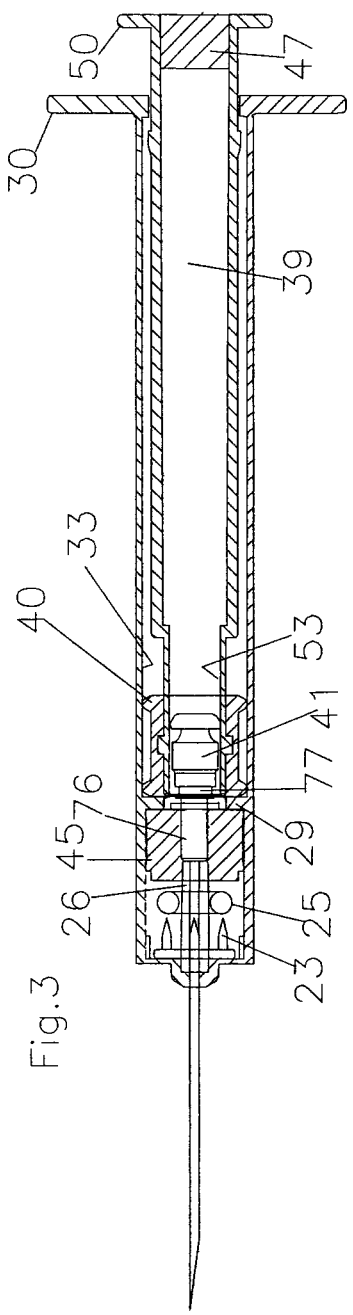
FIG. 3, in longitudinal section view, illustrates the syringe of FIG. 2 with the plunger having been depressed downstream to the position in which substantially all medicament drawn into the syringe barrel would have been expelled, the plunger has been locked within the barrel, and the needle port seal has engaged and sealed the needle aperture port in the needle header.

In the drawings and in this description, exemplary embodiments of syringes and syringe components made in accordance with various facets of the invention are illustrated. It is to be understood in this description that "the invention" may include a number of different inventive concepts and implementations, and that the words "the invention" may refer to one or more of them, as the context may require. The description and drawings illustrate representative embodiments of the invention and act as an aid to comprehension, and are not intended as a definition of the limits of the invention. The limits of the invention are as defined by the claims.

While in this specification, information is stated about materials selections and other parameters applicable to syringe designs according to the invention, (the syringes described herein had not gone into commercial production as of this writing), the reader should keep in mind that an empirical approach should be taken to the final design of any given syringe. Trade-offs always have to be made between design refinement and cost of manufacture. Tolerances can significantly affect the performance of a syringe made to certain specifications. Materials of a given specification will be not be identical to other materials meeting the same specification. Not all casting molds have identical surface smoothness. Et cetera. Testing and routine trial-and-error approaches should be expected to be a part of product development. Further, as all illustrations to which this description relates are schematic, the reader should not rely upon absolute nor relative dimensions that the eye may perceive in these illustrations.

In this specification, qualifying words should be taken in a relative sense, not an absolute sense. For example, if one element "seals" or "sealingly engages" another element, an absolute seal is not necessary; it suffices if enough sealing capability exists that the function for which the sealing is provided can be effectively performed by the syringe. As another example, locking the plunger "within the barrel of the syringe" should not be taken as implying that the full length of the plunger is within the barrel, but only that most of it is, so as to render the combined length of the external elements of the syringe reasonably compact. As yet another example, the fit of various components with one another is not intended to be precisely described; while to a careful engineer, there is a clear distinction between the concepts close fit, tight fit, and snug fit, nevertheless in this specification the fit of mating parts is described somewhat liberally, and "fit" should be considered relative to the purpose being served. The fit of a component with another for the purpose of a sealing engagement and no relative motion would be expected to be tighter than the fit of two components that must move with respect to one another. An empirical approach should be taken to syringe design based on guidelines in the description.

Further, while information is provided herein relative to the implementation of the inventions to which this specification is directed, no comprehensive nor consistent attempt is made in this specification to cover topics significant to syringe design generally but not specific to the present set of inventions. For example, the production molds for the syringe barrel have to be designed so that the syringe barrel can at all times maintain adequate sidewall pressure to allow the barrel to withstand full loading under expected peak injection force. Problems, solutions and design choices of the foregoing sort are well understood in syringe design. Suitable design choices would be empirically made by a competent syringe designer. However, please note, continuing the foregoing example, that the barrel design must be adequate to enable the barrel to maintain enough sidewall pressure for proper needle retraction—a point of information specific to the present set of syringe inventions. Representative gas cell pressures are set forth in this specification, so knowing these expected pressures, and providing a margin of tolerance, a competent syringe designer will be able to apply known strength-ofmaterials methodology to the materials selected for manufacture of the barrel, so as to enable the syringe to serve without expectation of failure.

In this description:

the concept "fixed" includes direct and indirect attachment and includes elements formed integrally with one another;

the concept "coupled" includes linking and cooperative association, but does not necessarily imply a fixed relationship;

"downstream" is the direction in which medicament flows during the injection phase of operation of the syringe, and may refer to a location that is nearer the tip of the needle than to the thumb and fingers of the user's hand;

"upstream" is the opposite of "downstream";

"axial" means along or in the direction of or parallel to the longitudinal axis of the syringe;

"radial" means perpendicular to axial, or in the direction of a radius of a circular or cylindrical element or configuration;

"distal" means at or toward the end of an element being described that is nearer the tip of the needle than to the thumb and fingers of the user's hand; and "proximal" is the opposite of "distal" and means at or toward the end of an element being described that is nearer the thumb and fingers of the user's hand than to the tip of the needle.

Referring first to FIGS. 1(a) and 1(b), there is illustrated in exploded longitudinal section view a retractable pneumatic safety syringe 20 in accordance with a first preferred embodiment of the invention. The syringe 20 has for the most part circular symmetry about its longitudinal axis. The principal gross elements of the syringe 20 are a syringe barrel or body 43, a plunger 48, and a needle assembly 82.

The hollow cylindrical syringe barrel 43 has a downstream compartment or chamber 32 and an upstream compartment or chamber 31 separated from one another by an annular separator wall 29 lying in a radial plane. The separator wall 29 has a central aperture 16. The upstream chamber 31 has an inner cylindrical wall surface 33 while the downstream chamber 32 has an inner cylindrical wall surface 28. The upstream end of the syringe barrel 43 is formed as or attached to flange 30 that may be, for example, circular and annular in its radial shape or alternatively may comprise opposed projecting tabs serving as finger grips. The flange 30 has a central access port opening or aperture 34 of slightly smaller diameter than the interior diameter of syringe barrel 43. Thus, the flange 30 extends radially inwardly from inner cylindrical surface 33 of the syringe barrel 43 to provide an interior bearing surface against which plunger lock verge 70 can bear, as discussed further below. The syringe barrel 43 also has a downstream barrel opening 38. The openings 16, 34 and 38 are axially aligned.

The hollow cylindrical plunger 48 has a hollow plunger body 72 configured and dimensioned to mate with and slide with limited axial movement within the upstream chamber 31 of the syringe barrel 43. The needle assembly 82 terminates at its distal end in a needle 37 that retracts into a retraction lumen 39 within the body 72 of the plunger 48 after use, as will be described in further detail below. The plunger body 72 is bounded by an inner cylindrical surface 54 and an outer cylindrical surface 57, a circumferential upstream plunger end flange 50 having a plug opening 51 for a plunger plug 47, and a downstream hollow cylindrical plunger end 52 and adjacent integral hollow neck 59. A circumferential collar 55 intervenes between the plunger end 52 and the adjacent neck 59. Apart from the collar 55, he end 52 and neck 59 have the same inner and outer diameters. The end 52 and neck 59 have appreciably smaller inner and outer diameters than those of the body 72 of the plunger 48; however, FIG. 1(b) exaggerates the expected difference in diameters. The diameter of the outer cylindrical surface 57 of the plunger body 72 is dimensioned so that the plunger body 72 fits slideably within the syringe barrel 43 with a tolerance selected to constrain the plunger 48 from rattling within the syringe barrel 43 and to constrain the plunger body 72 to slide within the syringe barrel 43 with a small frictional resistance to longitudinal displacement of the plunger body 72 within the syringe barrel 43.

The upstream plunger end flange 50 provides a bearing surface for two fingers on the downstream side thereof, permitting the user to withdraw the plunger 48 from the syringe barrel 20 when drawing medicament into chamber 74. Thumb pressure applied to the distal end surface of the plug 47 may be applied to move the plunger 48 downstream from an extended position. This configuration, combined with the flange 50 against which counterforce from two fingers may be applied, is sometimes referred to as a "thumb grip". The upstream outer end of the plug 47 may optionally be formed as a thumb cradle or concave thumb button; compare thumb cradle 651 of FIG. 6(a). The plug opening 51 is dimensioned and configured to permit the plunger plug 47 to penetrate part way into the plug opening 51 but to run into increasing interference as the plunger plug 47 is pushed into the plug opening 51. The plug opening 51 permits tools (not shown) to be inserted to access the internal parts of the syringe 20 during assembly thereof in order to facilitate assembly of the component parts of the syringe 20.

The downstream plunger neck 59 has a cylindrical inner surface 53. The internal diameter of the downstream plunger neck 59 is chosen such that a needle port seal 41 frictionally engages the inner surface 53 of the downstream plunger neck 59 with a fit approaching snug fit but permitting the needle port seal 41 to be driven upward in to the lumen 39 under gas pressure. At least the outermost circumferential portion of the needle port seal 41 is made of resilient material so that the needle port seal 41 may expand in diameter to fill the full cross-section of the lumen 39 when the needle port seal 41 enters the lumen 39 during the needle retraction phase of syringe operation.

A hollow deformable plunger seal 40 surrounds the downstream plunger end 52 and plunger neck 59 (see FIG. 2) with a snug or tight fit and is retained in position by means of the collar 55 that engages a mating annular recess 58 within the plunger seal 40. The dimensions and material of the plunger seal 40 are selected so that the plunger seal 40 slideably engages the inner cylindrical wall surface 33 of the upstream chamber 31 of the syringe barrel 43 with a fit approaching a snug fit permitting the plunger 48 to slide within the barrel 43 but with a modest frictional resistance. The relatively snug fit impedes leakage of fluid (such as medicament present in the available medicament cavity 74 within chamber 31 or air), past the plunger seal 40 of the plunger 48, while permitting longitudinal (axial) displacement of the plunger body 72 within the chamber 31.

The dimensions of the separator wall 29 and its aperture 16 are selected so that downstream motion of the plunger seal 40 is stopped when the seal 40 abuttingly engages the upstream side of the separator wall 29, whereas the cylindrical plunger end 52 and neck 59 downstream of the seal 40 may pass through the central aperture 16 of the separator wall 29 thereby allowing the distal cylindrical plunger end 52 to penetrate into the downstream chamber 32 of the syringe barrel 43. At the same time that the distal cylindrical plunger end 52 penetrates into the downstream chamber 32, the plunger seal 40 is forced slidingly upstream on the plunger neck 59 until the upstream motion of the plunger seal 40 is stopped by the engagement of the plunger seal 40 against an annular shoulder 56 formed at the upstream end of the neck 59.

Referring to FIGS. 1(a), 1(b), and 2, an engagement ring 45, having a central cylindrical opening 49, slideably but frictionally engages the inner cylindrical wall surface 28 of the downstream chamber 32 of the syringe barrel 43 with which surface 28 the engagement ring 45 is dimensioned and configured to mate. The engagement ring 45 may move axially within the downstream chamber 32, and in rest position the upstream end of engagement ring 45 abuts against the separator wall 29. When the plunger 48 is fully extended upstream out of the syringe barrel 43, as seen in FIG. 2, the engagement ring 45 is at rest in the chamber 32, whereas the plunger seal 40 and needle port seal 41 are at the upstream end of the chamber 31. The engagement ring 45 will not move from its rest position as seen in FIG. 2 until the end of the injection phase when downstream pressure applied to the plunger 48 by the user causes the downstream plunger end 52 to pass downstream through the aperture 16 of the separator wall 29, whereafter further downstream displacement of the plunger end 52 forces the engagement ring 45 to slide axially downstream.

Fully assembled, the needle assembly 82 comprises the needle port seal 41, a hollow needle header 42, and the hollow needle 37. The needle port seal 41 by itself or in combination with the needle header 42 constitute the needle carrier that is propelled by compressed gas into the plunger lumen 39 after injection. The diameter of the inner cylindrical surface 53 is selected relative to the outer diameter of the needle assembly 82 so that the needle assembly 82 may pass through the neck 59 of the plunger 48 into the lumen 39 of the plunger 48. Also, the length of the lumen 39 is selected relative to the length of the needle assembly 82 such that the needle assembly 82 can be housed completely within the lumen 39 after use.

The needle header 42 has a downstream hollow cylindrical body 76, a collar 77 and an upstream hollow end knob 78. The needle 37, having a downstream tip 36 and an upstream intake opening 75, is crimped in or cemented to or otherwise securely fixed within the body 76 of the needle header 42. The needle header 42 is dimensioned and configured such that during assembly of the syringe 20, the body 76 of the needle header 42 may be inserted into the central cylindrical opening 49 of the engagement ring 45, on the upstream side thereof, with a fit approaching a snug fit, thereby in its rest position impeding leakage of medicament contained in cavity 74 or other fluids between the needle header 42 and the engagement ring 45. In that rest position, the collar 77 abuts the upstream end of the engagement ring 45 to prevent the needle header 42 from passing downstream completely through the central cylindrical opening 49. The engagement ring 45 provides lateral support to the needle header 42, thereby stabilizing the needle 37 and its header 42 and enabling them to withstand the impact of pressure placed on the needle 37 during injection, especially if a muscle injection is made.

The dimensions and configuration of the knob 78 are such that the knob 78 engages in a snap fit a mating downstream socket 79 in the needle port seal 41 when, after injection of medicament from cavity 74 into a patient (say), the socket 79 of the needle port seal 41 is forced onto the knob 78 of the needle header 42 thereby securing the needle header 42 to the needle port seal 41, and thus prohibiting further escape of fluids through the needle 37.

When the syringe 20 is charged with medicament in cavity 74, the medicament is confineable within the upstream chamber 31 of the syringe barrel 43 downstream of the plunger seal 40 and needle port seal 41 (see FIG. 2), and upstream of the engagement ring 45 and needle header 42, also as shown in FIG. 2. The snug fit of the cylindrical surface of engagement ring 45 with the mating interior cylindrical surface 28 of the syringe barrel 43 acts as a barrier seal for medicament in cavity 74. The central opening 49 in the engagement ring 45 enables the engagement ring 45 to hold the needle header 42 and needle 37 in place and in alignment during injection of medicament from cavity 74 into the patient. It is important that the structure facilitate the alignment of the needle header 42 with the needle port seal 41. In one embodiment of the invention (as shown in FIGS. 1 to 4), the needle header 42 is situated within the engagement ring 45 in such a manner that the hollow knob 78 of the needle header 42 projects upstream of and out of the engagement ring 45, as illustrated in FIG. 2.

A hollow perforator 46 comprises a base 22, spaced puncture lance elements 23 fixed to the base 22 and projecting upstream therefrom, and an elongate central neck 26 projecting upstream from the base 22, the neck 26 having an inner cylindrical opening 24. The perforator 46 is positioned downstream of the engagement ring 45. The base 22, puncture lances 23 and the neck 26 of the perforator 46 may be machined as a single piece. In the embodiment of the invention illustrated in FIGS. 1(a), 1(b) and 2, the perforator 46 is secured in position by laminating, cementing or otherwise affixing the base 22 of the perforator 46 to a perforator mount 69. In this embodiment of the invention, the dimensions and material of the base 22 of the perforator 46 are preferably selected so that the base 22 of the perforator 46 may mate with the upstream end of the perforator mount 69 in a tight fit, thereby impeding leakage of gases or other fluids downstream. The perforator mount 69 is laminated, cemented or otherwise affixed to the inner wall 28 of the chamber 32 in the vicinity of the downstream barrel opening 38 of the syringe barrel 43. The perforator 46 and the engagement ring 45 are axially positioned, with respect to each other, within the downstream chamber 32 of the syringe barrel 43 in such a manner that the neck 26 of the perforator 46 is inserted into the central cylindrical opening 49 of the engagement ring 45. The neck 26 of the perforator 46 extends upstream and into the central cylindrical opening 49 of the engagement ring 45 to such an extent that the neck 26 of the perforator 46 contacts the body 76 of the needle header 42.

The needle 37 extends downstream from the needle header 42 and through the inner cylindrical opening 24 of the perforator 46 such that the downstream tip 36 of the needle 37 projects out of and downstream of the perforator 46. The neck 26 of the perforator 46 inhibits downstream motion of the needle header 42 or needle 37. The needle header 42 will not move until the plunger 48 has completed its downward motion, at the end point of which the socket 79 of the needle port seal 41 becomes attached to the needle header 42.

An annular gas cell 25, dimensioned and configured to fit within the downstream chamber 32 of the syringe barrel 43, is positioned within the downstream chamber 32 between the perforator 46 and the engagement ring 45. The gas cell 25 has a central inner opening 27 and contains a suitable non-toxic compressed gas in its interior gas chamber 80. The gas cell 25 is positioned such that the neck 26 of the perforator 46 projects through the inner opening 27 of the gas cell 25 thus facilitating proper alignment of the gas cell 25 with respect to the puncture lances 23 of the perforator 46 and facilitating proper alignment of the gas cell 25 with respect to the engagement ring 45. The material of the gas cell 25 is selected such that when the gas cell 25 is forced (with a typical hand pressure of approximately 6 p.s.i.g.) onto the puncture lances 23, the gas cell 25 is ruptured by the puncture lances 23.

The perforator mount 69 has a needle aperture 35 (FIG. 2) and is provided with a needle port closing membrane 68 fixed to the perforator mount 69 in the vicinity of the needle aperture 35. The membrane 68 is preferably a self-sealing membrane of the sort described in the referenced Klippenstein U.S. Pat. No. 5,868,713 at column 4, lines 27-37. The membrane 68 can be made of resilient material such as soft surgical-grade rubber of the type used in some medication bottles. When the membrane 68 is cast into shape, it is preferably formed with a small slightly coned hole that has about a 30° taper relative to the syringe's longitudinal axis to facilitate passage of the needle 37 through the membrane 68 during assembly and to facilitate needle retraction after syringe use. When the needle is retracted into the plunger, since the material is very soft, it tends to flow into itself and seal the hole. The needle 37 is mounted such that it passes through the inner cylindrical opening 24 of the perforator 46, and projects out of and downstream of the needle aperture 35. The needle aperture 35 is dimensioned to fit the needle 37 and help stabilize the needle 37 during injection of medicament. In order to impede leakage of compressed gas from the needle aperture 35, the needle membrane 68 tightly embraces the needle 37 where the needle 37 passes through the needle aperture 35. Once the needle 37 has been retracted into the lumen 39, the opening in the membrane 68 closes at least partially so that the needle membrane 68 covers the needle aperture 35 at least partially so as to impede downstream re-emergence of the needle 37 through the needle aperture 35.

During assembly of the components of the needle assembly 82, the upstream end of the needle 37 (in the vicinity of the intake opening 75) slides into and is secured in the body 76 of the needle header 42 by compression, cementing, or other suitable means. During injection, the fluid to be injected passes into the needle 37 through the hollow knob 78 of the needle header 42. The knob 78 is in this phase out of contact with the mating socket 79 in the needle port seal 41. It is not until after substantially all the medicament has been pushed out of the syringe 20 through the needle 37 that the knob 78 engages and is stopped by the socket 79.

Figure 4:
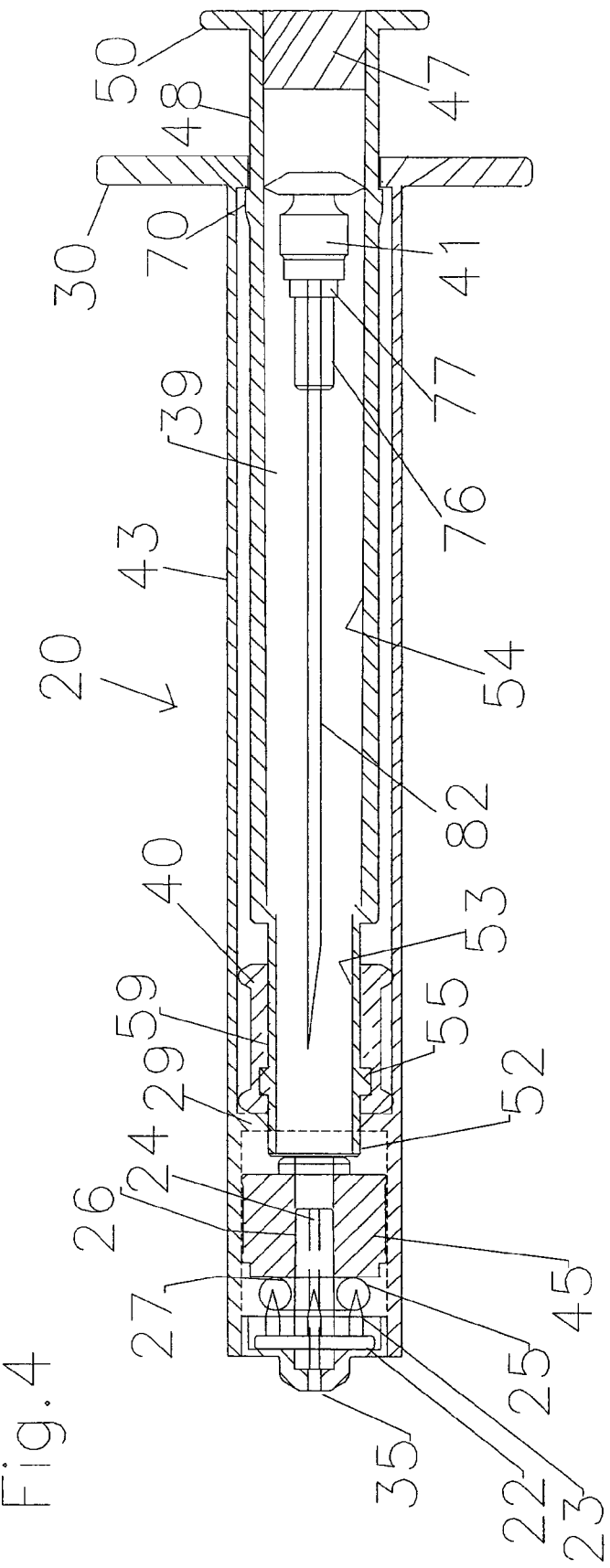
FIG. 4, in longitudinal section view, illustrates the syringe of FIG. 3 wherein the needle, needle header and needle port seal are shown as having been retracted within the retraction lumen of the plunger.

Referring to FIG. 2, the lumen 39 is bounded by the needle port seal 41, the upstream plunger end 50 and the inner surface 54 of the body 72 of the plunger 48. The lumen 39 is dimensioned and configured to house the needle assembly 82 after administration of the medicament from cavity 74 is complete and the needle assembly 82 has been retracted into the lumen 39. After assembly of the syringe 20, the plunger plug 47 is inserted into the plug opening 51, thus sealing the proximal upstream end of the lumen 39 of the plunger 48. Because the needle port seal 41 engages the inner surface 53 of the downstream plunger end 52 with a relatively snug fit, the needle port seal 41 prevents or inhibits leakage of medicament from cavity 74 past the needle port seal 41 into the lumen 39 during administration of medicament. In this embodiment of the invention, the needle port seal 41 is mounted such that in the fully extended position of the plunger 48, the downstream end of the needle port seal 41 projects downstream and out of the downstream plunger end 52 of the plunger 48. Referring to FIG. 4, during the needle retraction phase of operation of the syringe 20, the needle port seal 41 is forced upstream into the lumen 39 of the plunger 48. The diameter of the lumen 39 is chosen such that, under an upstream biasing pressure sufficient to overcome the frictional force between the needle port seal 41 and the inner surface 53 of the downstream plunger end 52, the needle port seal 41 is forced axially within the lumen 39 until further upstream movement of the needle port seal 41 is impeded by the plunger plug 47. The dimensions of the needle port seal 41 are selected so that the needle port seal 41 frictionally engages the inner surface 54 of the body 72 of the plunger 48.

Referring to FIGS. 1(b) to 4, in this preferred embodiment of the invention, the syringe 20 further includes a plunger lock comprising a plunger lock engagement element and a syringe barrel lock engagement element acting together that, after use of the syringe 20, constrain the plunger 48 to remain at or close to its downstream limit of travel. In other words, the plunger lock for the syringe 20 comprises an engagement element on the plunger 48 and another cooperating engagement element on the syringe barrel 43 that, at the downstream limit of travel of the plunger 48, lock the plunger 48 in place within the syringe barrel 43. In the embodiment illustrated in these figures of the drawings, the lock element of the plunger 48 is a plunger verge 70 formed as a raised circumferential ridge on the outer peripheral surface 57 of the plunger body 72 in the vicinity of the upstream end thereof. The lock element of the syringe barrel 43 comprises the inwardly extending verge of the end flange 30, whose interior diameter, i.e. the diameter of end flange port hole 34, is less than the outer diameter of the plunger verge 70. The plunger verge 70 has an inclined surface progressively increasing in diameter from its downstream limit to its upstream limit, and terminating in an upstream shoulder. In other words, the plunger verge 70 is configured to have a shallow downstream side and a steep upstream side (which latter can have a generally radial surface) such that when the plunger verge 70 is just upstream of the flange 30, a downstream force applied to the plunger permits the shallow downstream side of the plunger 48 to move downstream through the opening 34, but once the plunger verge 70 has been displaced downstream of the flange 30, the user will find it difficult or impossible thereafter to force the plunger 48 upstream, as the shoulder of the plunger verge 70 will bear substantially immovably against the inner circumferential surface of the flange 30, thereby locking the plunger 48 within the syringe barrel 43 after injection has been completed.

In a preferred embodiment of the invention, as shown in FIG. 1(a), a needle cover 44 is laminated, cemented or otherwise affixed to the downstream end of the perforator mount 69 in such a manner as to enclose the needle 37 thereby providing a protective sheath for the needle 37. In such an embodiment, the needle cover 44, prior to use, may be twisted off, snapped off, or otherwise removed from the perforator mount 69 without causing damage to the needle 37, the needle aperture 35 or the perforator 46, and thus exposing the needle 37 projecting through and downstream of the needle aperture 35, as shown in FIG. 2.

In operation, the syringe 20 is charged with medicament into cavity 74 in the same manner as a conventional syringe is charged with medicament. FIG. 2 illustrates, in a sectional view, the syringe 20 of FIGS. 1(a) and 1(b) wherein the needle cover 44 has been twisted off or otherwise removed from the perforator mount 69, thus exposing the needle 37 projecting downstream and out of the needle aperture 35. A user applies a downstream force to the upstream plunger end 50 thereby causing the plunger 48 and plunger seal 40 to move axially downstream within the upstream chamber 31 of the syringe barrel 43. The downstream motion of the plunger seal 40 forces most of air that is contained in the syringe barrel 43 through the upstream intake 75 of the needle 37 and out of the downstream tip 36 of the needle 37. When nearly all of the air is forced out of the syringe barrel 43, but before the plunger verge 70 engages the flange 30, the downstream tip 36 of the needle 37 is submerged into medicament contained in a supply vial (not shown). While maintaining submersion of the tip 36 of the needle 37 in the medicament an upstream force is applied to the plunger 48 thereby effectuating withdrawal of the medicament from the supply vial (not shown) and into the syringe barrel 43. Once the medicament is within the cavity 74 of the syringe barrel 43, the syringe 20 is held such that the downstream tip 36 of the needle 37 is pointed skyward such that any residual air floats above the medicament in the syringe barrel 43 whereafter a downstream force is applied to the plunger 48 such that the residual air is forced out of the syringe barrel 43. Referring to FIG. 2, when the syringe 20 is charged with medicament, the medicament is contained in cavity 74 entirely within the upstream chamber 31 of the syringe barrel 43 and confined between the plunger seal 40 of the plunger 48 and the engagement ring 45.

After the syringe 20 is charged with medicament, as shown in FIG. 2, a downstream injection force is applied to the plunger 48 to force the plunger 48 to slide axially downstream thereby forcing medicament from cavity 74 into the needle header 42 and discharging medicament through the needle 37. When a user applies a downstream injection force to the plunger 48, the plunger seal 40 at the downstream plunger end 52 imparts a downstream biasing pressure to the medicament in cavity 74 between the plunger seal 40 and the engagement ring 45. This downstream biasing pressure applied to the plunger 48 by the user is sufficient to force medicament through the upstream intake 75 of the needle 37 and into a patient via the downstream tip 36 of the needle 37. Although the medicament while being injected is placed under pressure by the plunger 48 and therefore exerts a downstream biasing pressure on the engagement ring 45, the resulting force on the engagement ring 45 is not sufficient to overcome the frictional force securing the engagement ring 45 to the inner cylindrical wall surface 28 of the downstream chamber 32 of the syringe barrel 43. Nor is the concurrent upstream biasing pressure on the needle port seal 41 sufficient to overcome the frictional force between the needle port seal 41 and the inner surface 53 of the downstream plunger neck 59.

FIG. 3 illustrates in sectional view the single-use pneumatic retractable syringe 20 of FIG. 2 wherein substantially all the medicament has been injected into the patient from cavity 74, and the needle port seal 41 has engaged and sealed the needle header 42. After substantially all of the medicament has been thus discharged, continued application of the injection force causes the downstream socket 79 of the needle port seal 41 to be forced onto the upstream end knob 78 of the needle header 42 thereby sealing the needle header 42 such that no further medicament or other fluids may be forced through the upstream intake 75 of the needle 37 and delivered to the patient. When the needle port seal 41 engages and seals the needle header 42 the needle assembly 82 is formed comprising the needle port seal 41, the needle header 42 and the needle 37. Downstream motion of the needle assembly 82 is restricted once the body 76 of the needle header 42 contacts the neck 26 of the perforator 46. When the body 76 of the needle header 42 contacts the neck 26 of the perforator 46 projecting upstream of the perforator 46, downstream motion of the needle assembly 82 is prevented.

Referring to FIG. 4 illustrates, in a sectional view, the single-use pneumatic retractable syringe 20 of FIGS. 1(a), 1(b), 2, and 3. In the view of the syringe in FIG. 4, needle retraction is complete; the needle assembly 82 is retracted within the lumen 39 of the plunger 48 and the plunger 48 is locked within the syringe barrel 43. After all the medicament has been thus discharged, further downstream movement of the plunger seal 41 is restricted by the separator wall 29 of the syringe barrel 43. Continued application of the downstream injection force (now a post-injection force) applied by the user to the plunger 48 causes the downstream plunger end 52 to move axially downstream and through the central aperture 16 of the separator wall 29 and forces the downstream plunger end 52 to impinge on the engagement ring 45. The post-injection force applied by the user to the plunger 48 overcomes the frictional force between the engagement ring 45 and the inner cylindrical wall surface 28 of the downstream chamber 32 of the syringe barrel 43, thereby causing the engagement ring 45 to slide axially downstream within the downstream chamber 32 of the syringe barrel 43.

The engagement ring 45 serves several purposes, viz (a) by means of its engagement with the surrounding cylindrical wall surface 33 of the syringe barrel 43, it provides stability and provides a compression seal to impede unwanted spurious fluid flow;

(b) by means of the engagement of its central cylindrical opening 49 with the needle header 42, it holds the needle header 42 and needle 37 in place during injection of medicament into the patient;

(c) by means of the engagement of its central cylindrical opening 49 with the perforator neck 26 and the engagement of that neck 26 with the needle header 42, it prevents premature puncture of the gas cell 25 by the perforator 46;

(d) by means of the foregoing engagements, it facilitates radial alignment of the gas cell 25 and the perforator 46, promoting even positioning of the gas cell 26 relative to the puncture lances 23, which in turn facilitates optimal puncturing of the gas cell 25 at the end of the plunger 48 downstroke;

(e) it facilitates accurate alignment of the needle port seal 41 with the needle header 42, in turn facilitating precise connection of the needle port seal 41 to the needle header 42 and thereby facilitating precise retraction of the needle 37; and (f) by means of its engagement with and displacement of the gas cell 25 at the end of the plunger 48 downstroke, displacing the gas cell 25 downstream into rupturing contact with the perforator 46, it plays a part in effecting the release of compressed gas, thereby in turn causing retraction of the needle assembly 82 into the retraction lumen 39 of the plunger 48.

Further downstream force (the post-injection force) applied to the plunger 48 causes the engagement ring 45 to be forced onto the gas cell 25 thereby causing the gas cell 25 to slide axially downstream eventually resulting in the gas cell 25 impinging on the puncture lances 23 projecting upstream from the perforator 46. This impingement causes the puncture lances 23 to rupture the gas cell 25, thereby releasing the compressed gas from the gas cell 25 into the syringe barrel 43. The released gas remains under pressure and is confined within the syringe barrel 43 in the area confined by the base 22 of the perforator 46, the plunger seal 40 and the needle port seal 41. Its purpose is to provide an upstream biasing pressure within the syringe barrel 43 upstream of the base 22 of the perforator 46 with sufficient pressure to overcome the frictional force securing the body 76 of the needle header 42 within the central cylindrical opening 49 of the engagement ring 45. Further, the upstream biasing pressure is sufficient to overcome the frictional force between the needle port seal 41 and the inner surface 53 of the downstream plunger neck 59 of the plunger 48. The upstream biasing pressure acting on the needle port seal 41 biases the needle assembly 82 to slide upstream into the lumen 39 of the plunger 48, thereby effecting withdrawal of the needle 37 into the lumen 39 of the plunger 48.

During the needle retraction phase, the needle port seal 41 slideably engages the inner surface 54 of the body 72 of the plunger 48 coming to rest at the plunger plug 47, thus retracting the needle assembly 82 into the lumen 39 of the plunger 48. There has to be enough gas under pressure that the upstream biasing pressure is sufficient to generate enough force to cause the needle assembly 82 to move upstream through the required distance. A suitable pressure range for gas stored within the gas cell 25 is expected to be about 5 to about 20 p.s.i.g. and preferably not exceeding about 9 p.s.i.g.

As the downstream tip 36 of the needle 37 passes upstream and through the needle aperture 35, the tapered portion of the needle membrane 68 flattens to cover the needle aperture 35 thereby impeding re-extension of the needle 37.

When the gas cell 25 is ruptured releasing the compressed gas, the upstream biasing pressure resulting from release of the gas is insufficient to force the plunger verge 70 upstream of the upstream port 34 of the syringe barrel 43. Upstream displacement of the plunger 48 after use is prevented or inhibited by the plunger verge 70 that engages the inner circular edge of end flange 30 when the plunger 48 has reached its downstream limit, thereby locking the plunger 48 within the syringe barrel 43. Once the plunger 48 is so locked within the syringe barrel 43 and once the needle assembly 82 is retracted into the lumen 39 of the plunger 48, the needle 37 cannot be reused or cause bodily harm, and can be disposed of in a suitable manner.

Figure 5A:
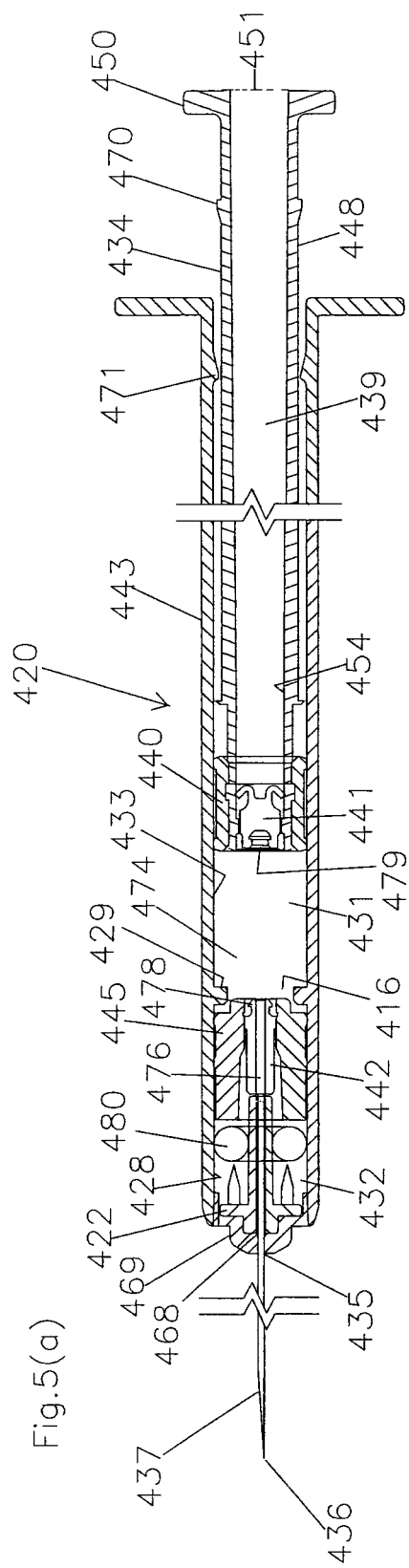
FIG. 5(a), in longitudinal section view, illustrates an alternative embodiment of a single-use pneumatic retractable syringe according to the invention wherein the engagement ring has been dimensioned and configured such that the needle header is positioned within a central cylindrical opening of the engagement ring, and showing the plunger as extending upstream partially out of the barrel.
Figure 5B:
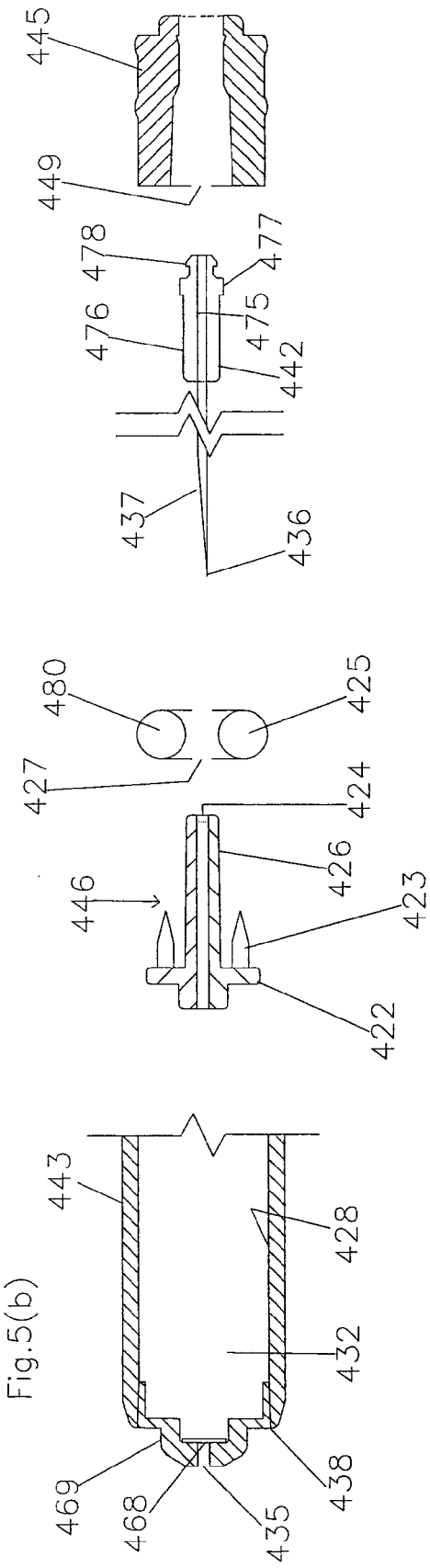
FIG. 5(b), in exploded longitudinal section fragment view, illustrates the downstream portion of the barrel of the syringe of FIG. 5(a) and associated interior components.
Figure 5C:
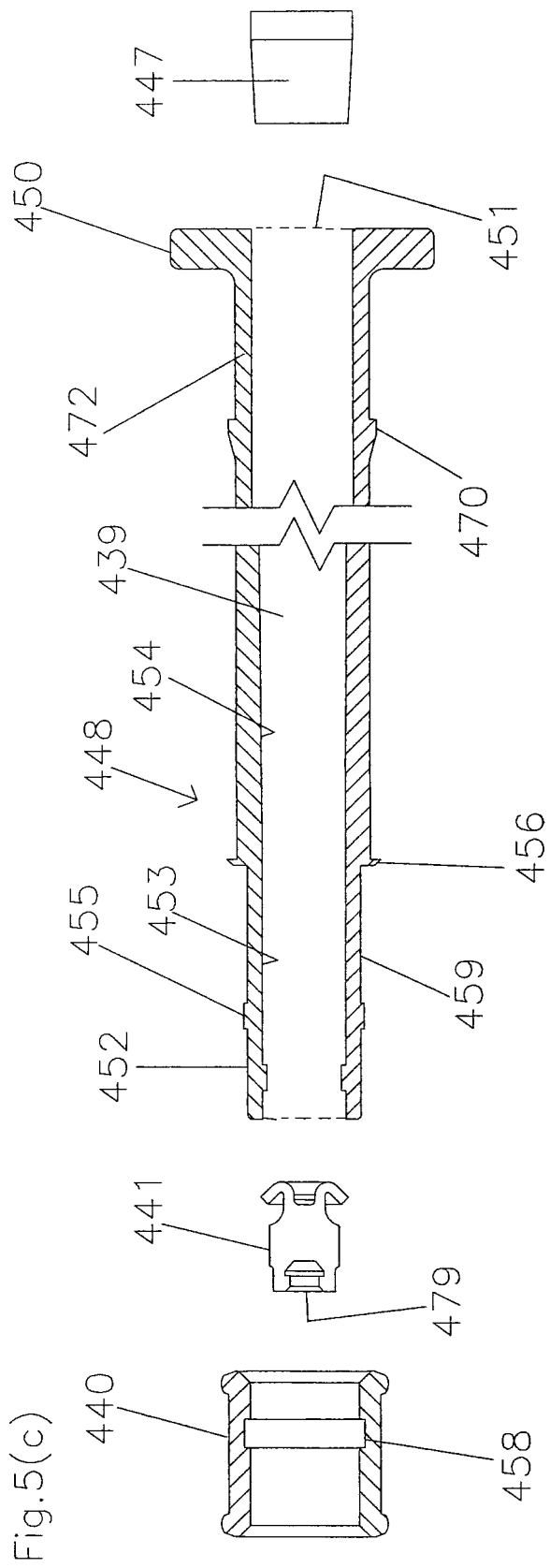
FIG. 5(c), in partially exploded longitudinal section fragment view, illustrates the plunger and associated components of the syringe of FIG. 5(a).

FIG. 5(*a*), in a sectional view, illustrates another embodiment of a single-use pneumatic retractable syringe wherein the engagement ring 445 has been dimensioned and configured such that a needle header, including the upstream end of the needle header, is positioned within the central cylindrical opening of the engagement ring 445. This embodiment of the invention differs in two major respects from the embodiment of the invention depicted in FIGS. 1 to 4, viz (i) the initial physical positioning of the needle header with respect to the modified engagement ring and (ii) the initial physical positioning of the needle port seal with respect to the plunger seal and the downstream end of the plunger. The modifications described below and depicted in FIGS. 5(*a-c*) allow for better alignment of the needle port seal with the needle header than may be readily achieved in the syringe of FIGS. 1 to 4.

The syringe 420 of FIGS. 5(*a-c*) comprises a hollow cylindrical syringe barrel 443 having a downstream chamber 432 and an upstream chamber 431 separated by an annular wall 429 lying in a radial plane, a flange 430 at the upstream extremity of the syringe barrel 443 having an upstream barrel opening 434 therein, and a downstream barrel opening 438 axially opposed to the upstream barrel opening 434. The annular wall 429 has a central aperture 416. The openings 416, 434, and 438 are axially aligned. The upstream chamber 431 has an inner cylindrical wall surface 433 while the downstream chamber 432 has an inner cylindrical wall surface 428.

A hollow cylindrical plunger 448 has a hollow plunger body 472 configured and dimensioned to mate with and slide within the upstream chamber 431 of the syringe barrel 443. A needle assembly (not shown) terminates at its distal end in a needle 437 that retracts into a lumen 439 within the body 472 of the plunger 448 after use, as will be described in further detail below. The body 472 of the plunger 448 is bounded by an inner cylindrical surface 454 and an outer cylindrical surface 457, an upstream plunger end 450 having a plug opening 451 for a plunger plug 447 (shown in FIG. 5(*c*)), and a downstream hollow cylindrical plunger end 452 and adjacent hollow neck 459 separated by external collar 455, the end 452 and neck 459 having the same inner and outer diameters and an appreciably smaller outer diameter than that of the body 472 of the plunger 448. The diameter of the outer cylindrical surface 457 of the body 472 is dimensioned so that the body 472 fits slideably within the syringe barrel 443 with a tolerance selected to constrain the plunger 448 from rattling within the syringe barrel 443 and to constrain the plunger body 472 to slide within the syringe barrel 443 with a small frictional resistance to longitudinal displacement of the body 472 within the syringe barrel 443.

The upstream plunger end 450 is flanged to provide a bearing surface for two fingers so that finger pressure thereon in combination with thumb pressure applied to the distal end surface of the plug 447 (shown in FIG. 5(*c*)) may be applied to grip the plunger 448, permitting the hand to move the plunger 448. The plug opening 451 is dimensioned and configured to permit the plunger plug 447 (shown in FIG. 5(*c*)) to penetrate part way into the plug opening 451 but to run into increasing interference as the plunger plug 447 (shown in FIG. 5(*c*)) is pushed into the plug opening 451. The plug opening 451 provides an opening whereby tools (not shown) can be inserted to access the internal parts of the syringe 420 during assembly thereof in order to facilitate assembly of the component parts of the syringe 420.

The downstream plunger neck 459 has a cylindrical inner surface 453. The internal diameter of the downstream plunger neck 459 is chosen such that a needle port seal 441 frictionally engages the inner surface 453 of the downstream plunger neck 459 with a snug fit but a fit permitting movement of the needle port seal 441 under gas pressure. In this embodiment of the invention, the needle port seal 441 is mounted in the downstream plunger end 452 such that the downstream distal end of the needle port seal 441 is flush with the distal end of the downstream end 452 of the plunger 448 (see FIG. 5(*a*)).

A hollow deformable plunger seal 440 surrounds the downstream plunger end 452 and the plunger neck 459 (see FIG. 5(*a*)) with a tight fit and is retained in position by means of the collar 455 that engages a mating annular recess 458 within the plunger seal 440. The fit, dimensions and material of the plunger seal 440 are selected so that the plunger seal 440 slidingly engages the inner cylindrical wall surface 433 of the upstream chamber 431 of the syringe barrel 443 with some resistance, thereby, (i) impeding leakage of fluid, such as medicament in cavity 474 or air, past the plunger seal 440 of the plunger 448, while (ii) permitting longitudinal displacement of the body 472 within the chamber 431. The dimensions of the annular wall 429 and its aperture 416 are selected so that downstream motion of the plunger seal 440 is stopped when the seal 440 abuttingly engages the annular wall 429, whereas the cylindrical plunger end 452 and neck 459 downstream of the seal 440 may pass through the central aperture 416 of the annular wall 429 thereby allowing the distal cylindrical plunger end 452 to penetrate into the downstream chamber 432 of the syringe barrel 443. At the same time that the distal cylindrical plunger end 452 penetrates into the downstream chamber 432 of the syringe barrel 443, the plunger seal 440 is forced slidingly upstream on the plunger neck 459 until the upstream motion of the plunger seal 440 is stopped by the plunger seal 440 engaging an annular shoulder 456 formed where the body 472 of the plunger 448 meets the neck 459.

Referring to FIGS. 5(*a-c*), a engagement ring 445, having a central substantially cylindrical opening 449, slideably but frictionally engages the inner cylindrical wall surface 428 of the downstream chamber 432 of the syringe barrel 443 with which surface 428 the seal 445 is dimensioned and configured to mate. The engagement ring 445 may move axially within the downstream chamber 432, and in rest position the upstream end of seal 445 abuts against the annular wall 429.

When the plunger 448 is fully extended upstream out of the syringe barrel 443, as seen in FIG. 5(a), the engagement ring 445 is at rest in the chamber 432, whereas the plunger seal 440 and needle port seal 441 are at the upstream end of the chamber 431. The engagement ring 445 will not move from its rest position as seen in FIG. 5(a) until the end of the injection phase when downstream pressure applied to the plunger 448 by the user causes the downstream plunger end 452 to pass downstream through the aperture 416 of the annular wall 429, whereafter further downstream displacement of the plunger end 452 forces the engagement ring 445 to slide axially downstream.

Fully assembled just prior to needle retraction, the needle assembly (not shown assembled) comprises the needle port seal 441, a hollow needle header 442, and the hollow needle 437. The needle port seal 441 by itself or in combination with the needle header 442 constitute the needle carrier. The diameter of the inner cylindrical surface 453 is selected relative to the outer needle port seal 441 so that the needle assembly may pass through the neck 459 of the plunger 448 into the lumen 439 of the plunger 448. Also, the length of the lumen 439 is selected relative to the length of the needle assembly such that the needle assembly can be housed completely within the lumen 439 after use. During the injection phase, the needle header 442 is positioned within the engagement ring 445 such that the knob 478 of the needle header 442 is flush with the upstream end of the engagement ring 445 (as seen in FIG. 5(a)). The needle header 442 has a downstream hollow cylindrical body 476, a collar 477 and an upstream hollow end knob 478. The needle 437, having a downstream tip 436 and an upstream intake opening 475, is cemented to or otherwise affixed within the body 476 of the needle header 442.

When the syringe 420 is charged with medicament, the medicament is confineable within the upstream chamber 431 of the syringe barrel 443 downstream of the plunger seal 440 and needle port seal 441 and upstream of the engagement ring 445 and needle header 442 as shown in FIG. 5(a). The engagement ring 445 provides a containment surface for the medicament within cavity 474 and maintains a compression seal to hold the needle header 442 and needle 437 in place during injection of medicament into the patient. In the embodiment of the invention shown in FIG. 5(a-c), the dimensions of the engagement ring 445 are selected so that the needle header 442 is surrounded by the engagement ring 445 in such a manner that the hollow knob 478 of the needle header 442 is flush with the upstream end of the engagement ring 445. In this embodiment, the needle port seal 441 is configured such that the distal end of the needle port seal 441 may be inserted into the central cylindrical opening 449 of the engagement ring 445 thus facilitating accurate alignment of the socket 479 of the needle port seal 441 to the knob 478 of the needle header 442. The engagement ring 445 maintains accurate positioning of the needle header 442 within the syringe barrel 443 so as to align the needle header 442 with the needle port seal 441.

A hollow perforator 446 comprising a base 422, spaced puncture lances elements 423 fixed to the base 422 and projecting upstream therefrom, an elongate neck 426 projecting upstream from the base 422, and having an inner cylindrical opening 424, is positioned downstream of the engagement ring 445. An annular gas cell 25 intervenes axially between the engagement ring 445 and the perforator 446. The base 422, puncture lances 423 and the neck 426 of the perforator 446 may be machined as one piece. In the embodiment of the invention shown in FIG. 5(a), the perforator 446 is secured in position by laminating, cementing or otherwise affixing the base 422 of the perforator 446 to a perforator mount 469. In such an embodiment of the invention, the dimensions and material of the base 422 of the perforator 446 are preferably selected so that the base 422 of the perforator 446 may mate with the upstream end of the perforator mount 469 in a tight fit, thereby impeding leakage of gases or other fluids downstream thereof. The perforator mount 469 is laminated, cemented or otherwise affixed to the inner wall 428 of the chamber 432 in the vicinity of downstream barrel opening 438 of the syringe barrel 443. The perforator 446 and the engagement ring 445 are axially positioned, with respect to each other, within the downstream chamber 432 of the syringe barrel 443 in such a manner that the neck 426 of the perforator 446 is inserted into the central cylindrical opening 449 of the engagement ring 445. The neck 426 of the perforator 446 extends upstream and into the central cylindrical opening 449 of the engagement ring 445 to such an extent that the neck 426 of the perforator 446 touches the body 476 of the needle header 442. The needle 437 extends downstream from the needle header 442 and through the inner cylindrical opening 424 of the perforator 446 such that the downstream neck 436 of the needle 437 projects out of and downstream of the perforator 446. The neck 426 of the perforator 426 prevents downstream motion of the needle header 442 or needle 437. The needle header 442 will not move until the plunger 448 has completed its downward motion, at the end point of which the needle port seal 441 is fixed to the needle header 442.

An annular gas cell 425, dimensioned and configured to fit within the downstream chamber 432 of the syringe barrel 443, is positioned within the downstream chamber 432 between the perforator 446 and the engagement ring 445. The gas cell 425 has an central inner opening 427 and contains a suitable non-toxic compressed gas in its gas storage chamber 480. The gas cell 425 is positioned such that the neck 426 of the perforator 446 projects through the inner opening 427 of the gas cell 425 thus facilitating proper alignment of the gas cell 425 with respect to the puncture lances 423 of the perforator 446 and facilitating proper alignment of the gas cell 425 with respect to the engagement ring 445. The material of the gas cell 425 is selected such that when the gas cell 425 is forced (with a pressure of approximately 6 p.s.i.g.) onto the puncture lances 423, the gas cell 425 is ruptured by the puncture lances 423. The gas in the gas cell 425 is expected to be at a pressure within the range previously specified for the gas cell 25.

The perforator mount 469 has a needle aperture 435 and is provided with a needle membrane 468 serving as a needle port closure. The needle 437 is mounted such that it passes through the inner cylindrical opening 424 of the perforator 446, and projects out of and downstream of the needle aperture 435. The needle aperture 435 is dimensioned such that the needle 437 is held firmly during the injection phase. In order to impede leakage of compressed gas from the needle aperture 435, the needle membrane 468 preferably surrounds the needle 437 where the needle 437 passes through the needle aperture 435. The needle membrane 468 is essentially similar to the membrane 68 previously described. Once the needle 437 has been retracted, the needle membrane 468 covers the needle aperture 435 so as to impede downstream re-extension of the needle 437 through the needle aperture 435.

Note that the upstream intake opening 475 of the needle 437 terminates in the hollow knob 478 of the needle header 442. The needle 437 during assembly slides into and is secured in the body 476 of the needle header 442. During injection, the fluid to be injected passes into the needle 437 through the knob 478, which in this phase of syringe operation is out of contact with the mating socket 479 in the needle port seal 441. It is not until after substantially all the fluid has been pushed out of the syringe 420 through the needle 437 that the knob 478 engages and is stopped by the socket 479.

A lumen 439 within the body 472 of the plunger 448 is bounded by the needle port seal 441, the upstream plunger end 450 and the inner surface 454 of the body 472 of the plunger 448. After assembly of the syringe 420, a plunger plug 447 is inserted into the plug opening 451, thus sealing the lumen 439 of the plunger 448. Because the needle port seal 441 engages the inner surface 453 of the downstream plunger end 452 with a snug fit, the needle port seal 441 prevents or inhibits leakage of medicament past the needle port seal 441 into the lumen 439 during administration of medicament. In this embodiment of the invention, the needle port seal 441 is mounted such that in the fully extended rest position of the plunger 448, the downstream end of the needle port seal 441 is flush with the downstream distal end 452 of the plunger 448 (as shown in FIG. 5(a)). During the needle retraction phase of operation of the syringe 420, the needle port seal 441 is forced upstream into the lumen 439 of the plunger 448. The diameter of the lumen 439 is chosen such that, under an upstream biasing pressure sufficient to overcome the frictional force between the needle port seal 441 and the inner surface 453 of the downstream plunger end 452, the needle port seal 441 is forced axially within the lumen 439 until further upstream movement of the needle port seal 441 is impeded by the plunger plug 447. The dimensions and materials of the needle port seal 441 are selected so that the needle port seal 441 frictionally but slideably engages the inner surface 454 of the body 472 of the plunger 448.

The syringe 420 is provided with a plunger lock that generally resembles that described with reference to FIG. 1ff, but differing in that a plunger verge 470, generally resembling plunger verge 70 in previous figures of the drawings, engages not an end flange on the syringe barrel but instead an interior lock-mate circumferential ridge or verge 471 in the vicinity of the upstream end of the syringe barrel 443. Referring to FIGS. 5(a-c), the plunger verge 470 is located on the outer surface 457 of the plunger 458 and is configured to have an inclined surface leading to an upstream shoulder. The lock-mate verge 471 is shaped similarly to plunger verge 470 but in the opposite sense so that shoulder-to-shoulder locking will occur upon downstream displacement of the plunger 448 sufficient to place plunger verge 470 downstream of the lock-mate verge 471. Note that the gentle inclination of the two verges 470, 471 in opposite senses facilitates passage of the verges 470, 471 past one another as the plunger is moved downstream.

The operation of the embodiment of the invention depicted in FIG. 5(a-c) is analogous to the operation of the embodiment of the invention depicted in FIGS. 1(a) to 4.

Preferably, the syringe barrel 443 and plunger 448 are fabricated from ASTM D 788 acrylic. Other materials suitable for use in the syringe 420 include USP class V1, PP [polypropylene] and rubber (as suitably selected) for many of the parts (other than the needle, of course, which is not part of the syringe parse). The needle 437 is suitably made of needle tubing by Popper, selection types 304 Hypodermic tubing, from 6 G through 32 G (with burr-free ECG grinding), or equivalent from other manufacturers. The syringe barrel 443 is preferably treated with a medical grade lubricant such as Dow Corning™ 360 Medical Fluid. Suitably, the compressed gas used in the gas cell 425 is Suva 134a (DUPONT™) or medical-grade nitrogen. As standard in the industry, the syringe 420 and all the components of the syringe 420 are preferably sterilized before packaging by oxide (EtO) gas using a suitable four-phase process. The foregoing materials selections are also generally suitable for other embodiments of syringes made in accordance with the invention.

Dimensions of the component parts of the syringe 420 and of the other syringes described herein will vary depending upon the volume of the syringe required. As of the writing of this specification, no commercial syringe in accordance with the invention had been manufactured, so reliable dimension figures were not available. An empirical approach should be taken in developing a commercial model from the drawings and description herein provided.

Figure 6:
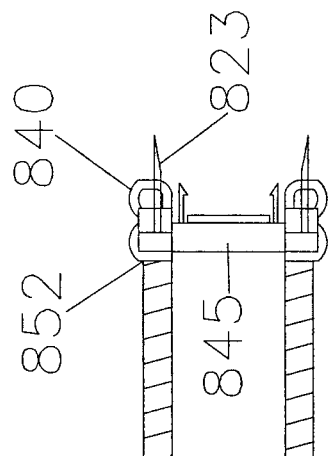
FIG. 6(a), in partially exploded longitudinal section view, illustrates a single-use pneumatic retractable syringe according to a further embodiment of the invention and a needle for use therewith.
FIG. 6(b) is a longitudinal section detail fragment view of the downstream plunger end of the syringe of FIG. 6(a).
FIG. 6(c) is a longitudinal section detail fragment view of an alternative embodiment of the downstream plunger end of the syringe of FIG. 6(a).
Figure 6:
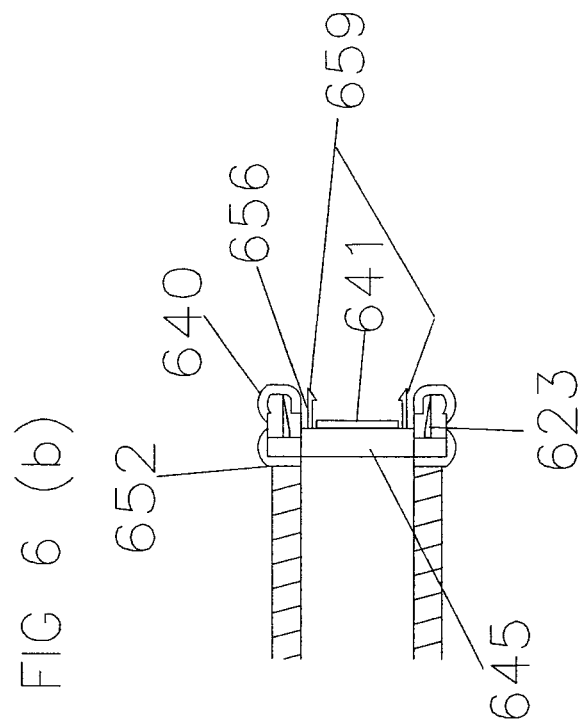

Referring to FIG. 6(a) and following figures, there is illustrated in an exploded cross-sectional view, a single-use pneumatic retractable syringe according to another embodiment of some aspects of the invention. This syringe more closely resembles the Klippenstein syringe of U.S. Pat. No. 5,868, 713 than does the embodiment of FIGS. 1-5, and the FIG. 6ff syringe does not embody some of the inventive characteristics of the syringe of FIGS. 1-5. The syringe 620 of this embodiment comprises a hollow cylindrical syringe barrel 643 having an inner cylindrical wall surface 633, an upstream barrel opening 634, and a downstream end 632 with a downstream barrel opening 638 axially opposed to the upstream barrel opening 634.

A plunger 648 is dimensioned, configured and positioned within the mating syringe barrel 643 for sliding axial movement within the syringe barrel 643. The plunger 648 is accordingly dimensioned to fit within the syringe barrel 643 within a tolerance permitting the plunger 648 to slide within the syringe barrel 643 while constraining the plunger 648 against rattling within the syringe barrel 643 and providing some frictional resistance to longitudinal sliding of the plunger 648 within the syringe barrel 643. The plunger 648 is hollow, having an inner surface 654 and an outer surface 657, an upstream plunger end 650 and a downstream plunger end 652. The upstream plunger end 650 is preferably capped with a thumb cradle or abutment 651.

An engagement disc 645 slidingly but frictionally engages the inner surface 654 of the plunger 648 at the downstream plunger end 652. The solid engagement disc 645 is dimensioned and configured to mate with the inner surface 654 of the plunger 648 at the downstream plunger end 652 and is positioned for axial movement within the plunger 648.

A lumen 639 within the plunger 648 is bounded by the engagement disc 645, the upstream plunger end 650 and the inner surface 654 of the plunger 648. The engagement disc 645 frictionally engages the inner surface 654 of the plunger 648, thereby impeding leakage of medicament from cavity 674 (shown in FIG. 8(a)) past the engagement disc 645 into the lumen 639 during administration of medicament. During the needle retraction phase, the engagement disc 645 is forced upstream into the lumen 639 of the plunger 648. The diameter of the lumen 639 is chosen such that, under an upstream biasing pressure sufficient to overcome the frictional force between the engagement disc 645 and the inner surface 654 of the plunger 648, the needle port seal 641 can move axially within the lumen 639 until further upstream movement of the needle port seal 641 is impeded by the thumb cradle 651. A slideable plunger seal 640 surrounds the downstream plunger end 652 and is affixed thereto. Optionally, the plunger seal 640 and the engagement disc 645 may be made as a unit with a scored or perforated edge between the engagement disc 645 and the plunger seal 640. The dimensions and material of the plunger seal 640 are selected so that the plunger seal 640 slidingly engages the inner cylindrical wall surface 633 of the syringe barrel 643 with a snug fit, thereby (i) impeding leakage of fluid, such as medicament past the plunger seal 640 of the plunger 648, while (ii) permitting longitudinal displacement of the plunger 648 within the syringe barrel 643 by means of normal hand pressure. During the needle retraction phase, the engagement disc 645 slidingly engages the inner surface 654 of the plunger 648, the engagement disc 645 coming to rest and frictionally engaging the inner surface 654 of the plunger 648 near the upstream plunger end 650 of the plunger 648 at the completion of the needle retraction phase.

A needle 637 for use in the syringe 620 has a generally disc-shaped needle header 642 integral with the upstream end thereof. The needle 637 and its header 642 have a central conduit for passage of medicament therethrough. A disc-shaped needle port seal 641 is affixed to the downstream end of the engagement disc 645. The needle port seal 641 may be constructed as a separate piece from the engagement disc 645, or the needle port seal 641 and the engagement disc 645 may be constructed as one piece. The purpose of the needle port seal 641 is to seal the upstream port of the medicament conduit in the needle 637 following injection.

A needle end cap 690 having an upstream end 692, a downstream end 694, and having formed within it needle aperture 635, is affixed to the downstream end 632 of the syringe barrel 643. The inner wall of the upstream end rim 692 of the needle end cap 690 is dimensioned and configured to mate with the outer cylindrical surface of the downstream end 632 of the syringe barrel 643 with a tight fit. For user convenience, the needle end cap 690 may be colour-coded to indicate needle size.

An alignment disc 646 is securely mounted in the needle end cap 690 near the upstream end 692 of the needle end cap 690 in such a manner that a gas cell compartment 696 is formed between the base of the alignment disc 646 and a circular recess formed in the needle end cap 690. The alignment disc 646 establishes an initial buffer between the gas cell 625 and the downstream end 652 of plunger 648. Optionally, an annular tension seal (not shown) may surround the alignment disc 646 to facilitate its secure mounting in the needle end cap 690.

A pair of diametrically spaced puncture lances 623 are affixed to the downstream plunger end 652 in alignment with spaced through-holes 658 in alignment disc 646, the through-holes 658 being dimensioned and affixed to the downstream plunger end 652 to pass therethrough. The number of through-holes 658 and corresponding puncture lances 623 is not limited to two, but preferably the through-holes 658 and corresponding puncture lances 623 should be arranged about the aperture 624 in a circular symmetrical manner. Note that it is essential to this embodiment that when the end cap 690 is assembled to the barrel 643, the alignment disc is oriented so that the through-holes 658 are aligned with the puncture lances 623.

As shown in FIGS. 6(a) and 6(b), the puncture lances 623 may be completely surrounded by the plunger seal 640. Alternatively, as shown in FIG. 6(c), a syringe may be constructed wherein a puncture lance 823 projects downstream and through a plunger seal 840. Optionally, the gas cell compartment 696 may be separately made unit surrounding the gas cell 625 but designed to permit ready access of the puncture lances 623 to the gas cell 625.

In the assembly of the syringe 620, prior to affixing the end cap 690 onto the syringe barrel 643, the needle 637 is mounted in the needle end cap 690 by passing the downstream end of the needle 637 through the central aperture 624 of the alignment disc 646, through the inner opening 627 of the gas cell 625, and through the needle aperture 635 in the needle end cap 690. The central aperture 624 of the alignment disc 646 and the needle aperture 635 of the needle end cap 690 are dimensioned and configured to embrace and support the needle 637 with a snug fit.

A needle header lock 656 is provided to provide, just before the end of the downstroke of the plunger 648, a locking engagement between downstream plunger end 652 and needle header 642. As illustrated, the header lock 656 comprises a pair of diametrically spaced barbed lances 659 affixed to the engagement disc 645 and projecting downstream therefrom. The barbed lances 659 are configured and dimensioned for locking engagement with the peripheral edge of the needle header 642; this is facilitated by a circular recess 655 in the alignment disc 646 permitting the lance points as they move downstream to bend outwardly and overshoot the peripheral edge of the needle header 642 and then to spring inwardly to grip the needle header 642 in a locking engagement. The diameter of the needle header 642 is selected such that the peripheral edge of the needle header 642 partially covers the circular recessed groove 655 in the alignment disc 646, facilitating retention of the header lock lances 659 by the needle header 642. Other suitable snap-fit or other locking engaging components could be substituted for those illustrated, but the illustrated arrangement is compact and effective.

Figure 7B:
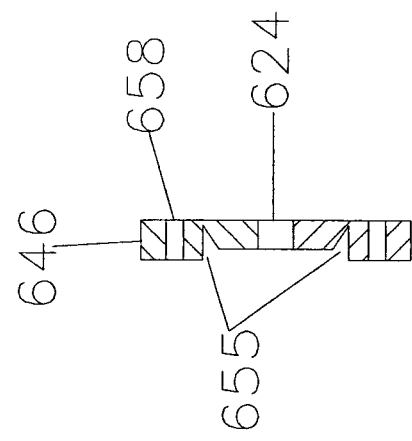
FIG. 7(b), in longitudinal section view, illustrates the alignment disc of FIG. 7(a).
Figure 7A:
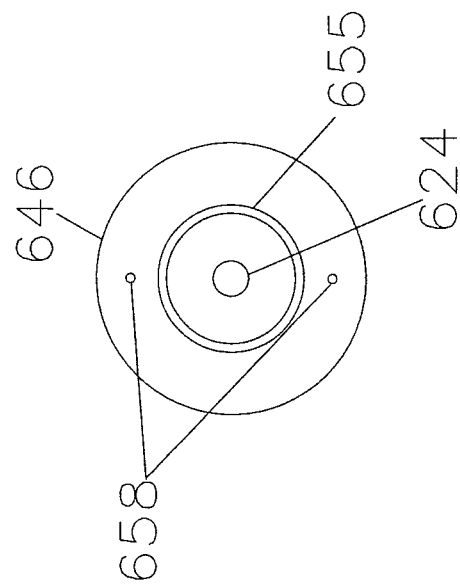
FIG. 7(a), in end view in the radial plane, illustrates the alignment disc of the syringe illustrated in FIG. 6(a).

FIG. 7(a) illustrates, in a plan view, and FIG. 7(b) illustrates, in a cross-sectional view, the alignment disc 646 according to the embodiment of the invention illustrated in FIG. 6(a). The alignment disc 646 is generally circular with a central aperture 624 dimensioned and configured to allow a hollow needle 637 to pass therethrough. A circular recessed groove 655 dimensioned and configured to receive the barbed lances 659 attached to the engagement disc 645 is concentric with the central aperture 624 of the alignment disc 646.

Reverting to FIG. 6(a), an annular gas cell 625 with an inner "doughnut hole" opening 627 and containing a suitable non-toxic compressed gas in its gas storage chamber 680 is dimensioned and configured to fit within the gas cell compartment 696. The material of the gas cell 625 is selected such that when the puncture lances 623 are forced (preferably with a pressure of approximately 6 p.s.i.g.) against the gas cell 625, the gas cell 625 is ruptured by the puncture lances 623.

In order to impede leakage of compressed gas from the needle aperture 635 of the needle end cap 690, an annular needle membrane 668 fixed to the needle end cap 690 surrounds the needle 637 at the upstream limit of the needle aperture 635 of the needle end cap 690. The membrane 668 is essentially similar to the membrane 68 previously described and serves as a needle port closure. Once the needle 637 has been retracted into the lumen 674 after use of the syringe, the needle membrane 668 covers the needle aperture 635 so as to impede downstream penetration of the needle 637 through the needle aperture 635.

In this embodiment of the invention, the syringe 620 further comprises a plunger verge 670 and a cooperating lock-mate verge 671 whose structure, location, and locking operation generally resemble those previously described with reference to plunger verge 470 and lock-mate verge 471.

Figure 8A:
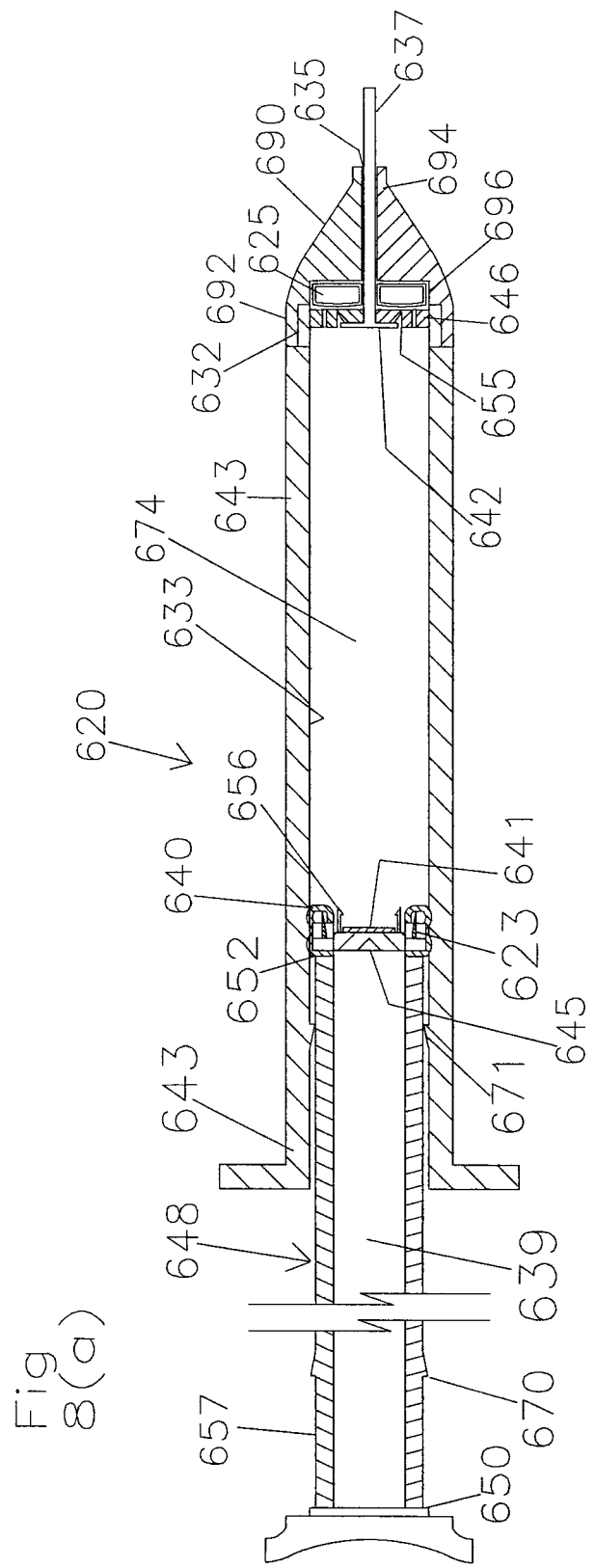
FIG. 8(a), in longitudinal section view, illustrates the syringe of FIG. 6(a) with the plunger partially extended upstream out of the syringe barrel.

Referring to FIGS. 8(a-c), in operation, the syringe 620 is charged with medicament in the same manner as a conventional syringe is charged with medicament. A user applies a downstream force to the upstream plunger end 650 thereby causing the plunger 648 and plunger seal 640 to move axially downstream within the syringe barrel 643. The downstream motion of the plunger seal 640 forces most of air that is contained in the syringe barrel 643 through the upstream intake of the needle 637 and out of the downstream tip of the needle 637. When nearly all of the air is forced out of the syringe barrel 643, but before the plunger verge 670 engages the lock-mate verge 671, the downstream tip of the needle 637 is submerged into medicament contained in a supply vial (not shown). While maintaining submersion of the tip of the needle 637 in the medicament, an upstream force is applied to the plunger 648 thereby effectuating withdrawal of the medicament from the supply vial and into the cavity 674 in the syringe barrel 643. Once the medicament is within the cavity 674, the syringe 620 is held such that the downstream tip of the needle 637 is pointed skyward such that any residual air floats above the medicament in the syringe barrel 643 whereafter a downstream force is applied to the plunger 648 such that the residual air is forced out of the syringe barrel 643. Referring to FIG. 8(a), when the syringe 620 is charged with medicament, the medicament is contained within the syringe barrel 643 and confined between the plunger seal 640 of the plunger 648, the engagement disc 645 and the alignment disc 646.

After the syringe 620 is charged with medicament, as shown in FIG. 8(a), a downstream injection force is applied to the plunger 648 to force the plunger 648 to slide axially downstream thereby forcing medicament into the needle header 642 and discharging medicament through the needle 637. When a user applies a downstream injection force to the plunger 648, the plunger seal 640 at the downstream plunger end 652 imparts a downstream biasing pressure to the medicament contained in the syringe barrel 643. This downstream biasing pressure applied to the plunger 648 by the user is sufficient to force medicament through the upstream intake of the needle 637 and into a patient via the downstream tip of the needle 637. Although the medicament while being injected is placed under pressure by the plunger 648 and therefore exerts a corresponding upstream biasing pressure on the engagement disc 645, the resulting force on the engagement disc 645 is not sufficient to overcome the frictional force securing the engagement disc 645 to the inner surface 654 of the plunger 648.

Referring to FIG. 8(b), after substantially all of the medicament has been thus discharged from the cavity 674, continued application of the injection force causes the downstream end of the needle port seal 641 to be forced onto the needle header 642 thereby sealing the needle header 642 such that no further medicament or other fluids may be forced through the upstream intake of the needle 637 and delivered to the patient. When the needle port seal 641 engages and seals the needle header 642 the barbed lances 659 project into the recessed groove 655 of the alignment disc 646. When a downstream force is applied to the plunger 648 the shallow downstream side of the barbed lances 659 is forced downstream of the outer edge of the needle header 642 and into the recessed groove 655 of the alignment disc 646. The barbs on the barbed lances 659 engage the needle header 642 and secure the needle header 642 thereto since the steep upstream side of the barbed lances cannot be forced upstream past the outer edge of the needle header 642.

Figure 8C:
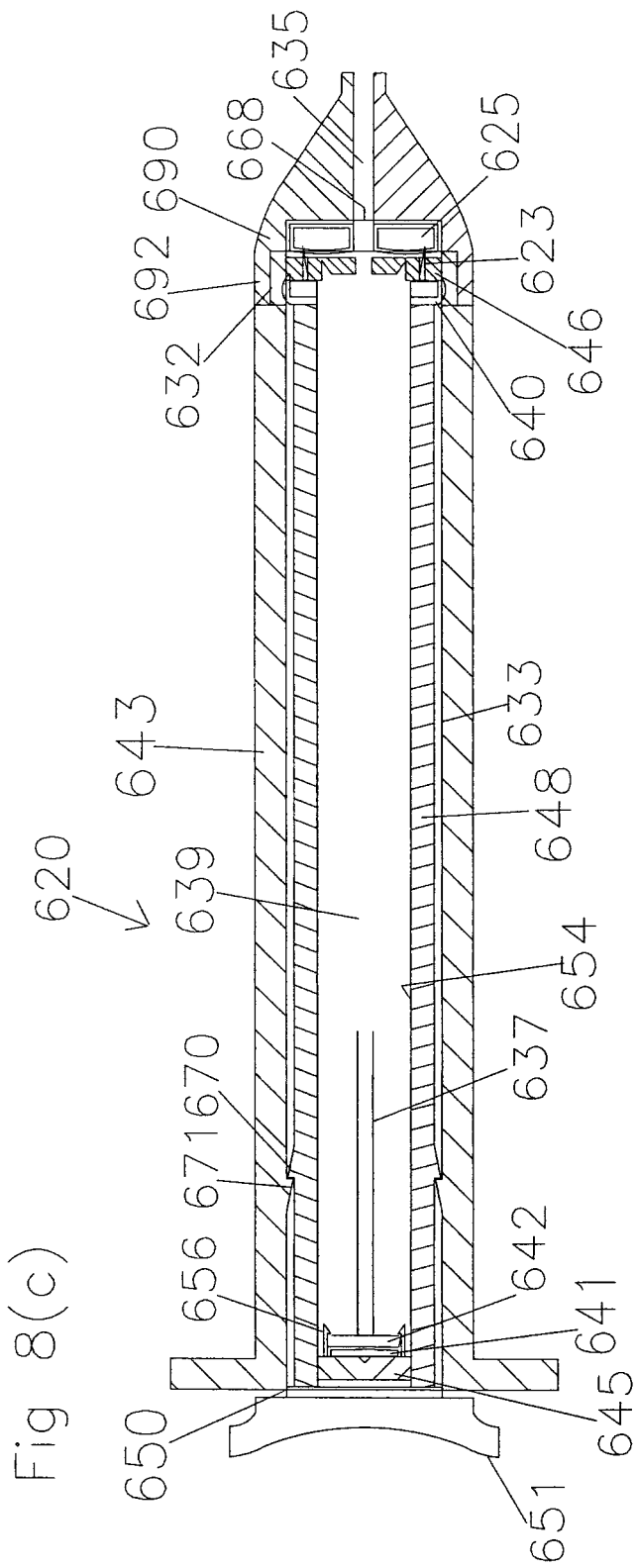
FIG. 8(c), in longitudinal section view, illustrates the syringe of FIG. 8(b) wherein the needle, needle header and needle port seal are shown as having been retracted within the retraction lumen of the plunger, and the plunger is locked within the syringe barrel.

Referring to FIG. 8(c), after all the medicament has been thus discharged from the cavity 674, continued application of the downstream injection force (now a post-injection force) applied by the user to the plunger 648 causes the puncture lances 623 to pass through the through holes 658 of the alignment disc 646 and forces the puncture lances 623 to impinge the gas cell 625. Forcing the puncture lances 623 onto the gas cell 625 causes the puncture lances 623 to rupture the gas cell 625, thereby releasing the compressed gas from the gas cell 625. The released gas escapes through holes 658 and biases the plunger 648 to move within the syringe barrel 633 in an upstream direction. Movement of the plunger 648 out of the syringe barrel 633 is, however, prevented or inhibited by the engagement of plunger verge 670 with the lock-mate verge 671. The released gas exerts an upstream biasing pressure within the syringe barrel 643 with sufficient pressure to overcome the frictional force between the engagement disc 645 and the inner surface 654 of the plunger 648 thus forcing the engagement disc 645 to slide axially upstream within the lumen 639 of the plunger 648. As the engagement disc 645 slides upstream in the lumen 639 it carries the needle 637 into the lumen 639 as the needle header 642 is secured to the engagement disc 645 by the barbed lances 659 thereby withdrawing the needle 637 into the lumen 639 of the plunger 648. (In this embodiment, the needle carrier comprises the combination of the engagement disc 645 with the header lock 656.) Of course, there has to be enough gas under pressure in storage chamber 680 that the upstream biasing pressure is sufficient to generate enough force to cause the needle 637 to move upstream through the required distance. The pressure of the compressed gas within the gas cell 625 is expected to be within the range previously specified for the gas cell 25.

At the end of the needle retraction phase, further upstream movement of the needle 637 is restricted by the thumb cradle 651. The engagement disc 645 frictionally engages the inner surface 654 of the plunger 648 near the upstream plunger end 650 of the plunger 648, thus retaining the needle header 642 and needle 637 within the lumen 639 of the plunger 648.

As the downstream tip of the needle 637 passes through the needle aperture 635, the tapered portion of the needle membrane 668 flattens to cover the needle aperture 635 thereby impeding re-extension of the needle 637.

When the gas cell 625 is ruptured, releasing the compressed gas from the gas storage chamber 680, the upstream biasing pressure resulting from release of the compressed gas is insufficient to force the plunger verge 670 upstream of the lock-mate verge 671 of the syringe barrel 643. Once the plunger 648 is so locked within the syringe barrel 643 and once the needle 637 is retracted into the lumen 639 of the plunger 648, the needle 637 cannot be reused or cause bodily harm, and can be disposed of in a suitable manner.

In all described embodiments of the inventive syringe, when gas forces the needle, needle header and other syringe components upstream into the plunger lumen, the air previously in the lumen will tend to become compressed. The compressed air may be released by providing a small vent hole (not illustrated) in the plunger wall, preferably located upstream of the plunger lock verge, thereby facilitating needle retraction.

Variations in what has been described and illustrated in this specification will readily occur to those skilled in the technology. A few examples of possible improvements, modifications and variants follow:

The volume of the lumen 39 bounded by the inner surface 54 of the plunger 48, the needle port seal 41 and the plug plunger 47 could be partially evacuated thereby aiding in the rapid retraction of the needle assembly 82 and allowing for a reduction in the gas pressure contained in the gas cell 25.

Instead of being penetrated by puncture lances 23, the gas cell 25 could be broken by being crushed by the plunger seal 40 or being torn away from the inner cylindrical wall surface 33 of the syringe barrel 43, thereby being torn open by the downstream movement of the plunger 48.

The puncture lances 23, instead of being mounted on the perforator 46 in such a manner that the puncture lances 23 project upstream from the perforator 46 towards the gas cell 25, could alternatively be mounted on a perforator fixed to (or, less desirably, placed immediately downstream of) the downstream end of the engagement ring 45 in such a manner that the puncture lances 23 project downstream from the engagement ring 45 towards the gas cell 25. In such alternative embodiment, the perforator 46 could be secured in position by laminating, cementing or otherwise affixing the base 22 of the perforator 46 to the inner cylindrical wall surface 28 of the syringe barrel 43. The fit or bonding of the circumferential periphery of the perforator to the interior of the syringe barrel should be effective to prevent or substantially impede leakage of gases or other fluids downstream of the perforator 46 other than through the needle.

The gas release cell, instead of containing pre-injection compressed gas, could contain chemically reactive liquids or possibly solids instead of gases in each of two or more subcompartments, each subcompartment containing a discrete reagent. The subcompartments could be separated from one another by one or more walls to be punctured. Upon puncturing the separating wall or walls, the reagents in the subcompartments would mingle and react so as to generate a gas under pressure, released when the cell is punctured. This alternative would be of some advantage in that such modified cell 25 would not be under any pressure until the syringe 20 is used.

The needle cover 44 and the perforator mount 69 could be manufactured as two distinct pieces and coupled together with a releasable holding means.

While it is considered preferable to manufacture and sell the syringe as a completely assembled article of manufacture, it is possible to manufacture and sell the syringe as a set of subassemblies. For example, the needle and needle header could be separately provided. The perforator and perforator mount in some embodiments could be sold detached from the barrel, and the gas cell could also be kept separate and installed just before use of the syringe, whereafter completion of assembly of the syringe could take place. Disadvantages of manufacture and sale of the syringe as a set of subassemblies include risk of damage to sensitive components such as the needle, risk of accidental stabbing, risk of premature rupture of the gas cell, and risk of misalignment of components. Advantages include the possibility of more compact packaging of the syringe for sale, and the possibility of separate packing of the gas cell, which could be packed within an outer container that is itself pressurized so as to reduce the stress on the gas cell wall or "skin" prior to use of the syringe.

Many mechanical expedients are known for interlocking two meshing or mating elements. Various of them could be selected in substitution for the plunger verge/lock-mate verge examples described and illustrated herein.

Many mechanical expedients are known for effecting support and alignment of components requiring such. Where radial alignment is required, the radial cross-section of aligned components can be non-circular, e.g. with one flattened side. Or tongue-and-groove alignment may be provided. Various alignment techniques could be selected in substitution for the alignment arrangements described and illustrated herein by way of example, and the same applies to support.

Many mechanical expedients are known for disabling elements after some mechanical event occurs. In the present case, it is an objective to disable the needle after use of the syringe, and to provide some means to prevent or inhibit its re-extension after it has been retracted into the plunger lumen. One means herein described for inhibiting needle re-extension is a resilient membrane located downstream of the needle header and through which the slender portion of the needle passes. After needle retraction has been completed, the membrane at least partially closes upon the aperture through which the needle has passed. But other means can be readily conceived for blocking the exit of the needle from the lumen, once it has been retracted.

Where components are to be secured to one another, some discretion is permitted to the designer and manufacturer. In many cases, tight-fit, snap-fit, twist-off, or threaded connection suffices, and may be preferred to gluing, as one may wish to avoid contact between glue and the interior of the syringe and particularly to avoid contact between glue and medicament to be injected.

The foregoing are exemplary only; other possible equivalents and substitutions will readily occur to those skilled in the mechanical design of hypodermic-needle-type syringes.

Accordingly, the invention is not to be limited by the specific embodiments described above; the scope of the invention is as defined in the claims.

What is claimed is:

1. A syringe having a retractable needle, the syringe comprising:
   a syringe barrel;
   a needle disposed at a distal end of the syringe barrel, the needle having a needle header at its proximal end;
   a plunger slideable within the syringe barrel for injecting medicament and having a retraction lumen for receiving the needle when the needle is retracted;
   a needle carrier sealingly engaged within a distal end of the plunger, the needle carrier having a distal bearing surface against which gas under pressure may bear and being initially retained in a fixed position relative to the plunger, the needle carrier being slideable within the retraction lumen in response to force applied by gas under pressure;
   a gas release cell located within the syringe barrel distally of the needle carrier; and
   gas release trigger means located within the syringe barrel distally of the needle carrier for rupturing the gas release cell in response to application of a post-injection force to the plunger by a user to release compressed gas in an area confined by the syringe barrel and the needle carrier,
wherein the needle carrier is engageable with the needle header to retract the needle into the plunger lumen under force applied by released gas when the gas release cell is ruptured.

2. A syringe as defined in claim 1, wherein the plunger comprises a plunger seal initially retained on a distal end of the plunger for injecting medicament, the plunger seal being displaceable in the proximal direction when the post-injection force is applied to the plunger by the user.

3. A syringe as defined in claim 2, comprising a radial separator wall disposed between an upstream chamber of the syringe containing medicament and a lower chamber of the syringe containing the gas release cell, wherein contact of a distal edge of the plunger seal with a proximal edge of the radial separator wall displaces the plunger seal in the proximal direction when the post-injection force is applied to the plunger by the user.

4. A syringe as defined in claim 3, wherein the plunger seal is initially retained on the distal end of the plunger by engagement of an outwardly projecting circumferential collar on the distal end of the plunger with a corresponding annular recess within an inside surface of the plunger seal.

5. A syringe as defined in claim 4, wherein the engagement of the circumferential collar on the distal end of the plunger with the corresponding annular recess within the inside surface of the plunger seal is broken when the plunger seal is displaced in the proximal direction when the post-injection force is applied to the plunger by the user.

6. A syringe as defined in claim 3, wherein the distal end of the plunger comprises a neck having a diameter smaller than a diameter of a body of the plunger, and wherein the neck is dimensioned to pass through the radial separator wall.

7. A syringe as defined in claim 6, wherein the plunger seal is initially retained on the neck.

8. A syringe as defined in claim 7, comprising an engagement ring frictionally engaged within the syringe distally of the plunger and proximally of both the gas release cell and the gas release trigger means, the engagement ring being initially retained in a fixed position and slideable in the distal direction upon the application of the post-injection force to the plunger by the user to cause the gas release trigger means to rupture the gas release cell.

9. A syringe as defined in claim 8, wherein, during the application of the post-injection force, a distal end of the neck of the plunger contacts a proximal portion of the engagement ring to slide the engagement ring in the distal direction.

10. A syringe as defined in claim 8, wherein the needle header is sealingly engaged within the engagement ring.

11. A syringe as defined in claim 10, wherein the needle header is situated within the engagement ring in such a manner that an upstream portion of the needle header projects proximally out of a central opening of the engagement ring.

12. A syringe as defined in claim 10, wherein the needle header engages in a snap fit with the needle carrier after injection of the medicament.

13. A syringe as defined in claim 12, wherein the needle carrier comprises rubber.

14. A syringe as defined in claim 1, additionally having a plunger lock for impeding or preventing removal of the plunger out of the barrel after use of the syringe.

15. A syringe as defined in claim 14, wherein the plunger lock comprises:
 a plunger lock engagement element fixed to the plunger; and
 a cooperating lock-mate engagement element fixed to the barrel;
wherein the engagement elements are located so as to make engaging contact with one another as the plunger is pushed downstream within the syringe; and
downstream motion of the plunger past the point of engaging contact causes the locking of the plunger within the barrel.

16. A syringe as defined in claim 1, wherein the plunger comprises a vent hole to release air from the retraction lumen during needle retraction.

17. A syringe as defined in claim 1, comprising a needle end cap secured over the needle.

18. A syringe as defined in claim 17, wherein the needle end cap is color-coded to indicate needle size.

19. A syringe as defined in claim 1, comprising a seal around the needle to prevent leakage of compressed gas past the needle in a distal direction when the gas release cell is ruptured.

20. A syringe as defined in claim 19, wherein the seal comprises a membrane.

* * * * *